(12) United States Patent
Corrie et al.

(10) Patent No.: US 8,188,225 B2
(45) Date of Patent: May 29, 2012

(54) INORGANIC PHOSPHATE ASSAYS

(75) Inventors: John Edgar Thomas Corrie, London (GB); Martin Ronald Webb, London (GB); Michael Prince Okoh, London (GB)

(73) Assignee: Medical Research Council, Swindon (GB)

( * ) Notice: Subject to any disclaimer, the term of this patent is extended or adjusted under 35 U.S.C. 154(b) by 859 days.

(21) Appl. No.: 11/990,847

(22) PCT Filed: Aug. 31, 2006

(86) PCT No.: PCT/GB2006/003228
§ 371 (c)(1),
(2), (4) Date: Aug. 4, 2008

(87) PCT Pub. No.: WO2007/026155
PCT Pub. Date: Mar. 8, 2007

(65) Prior Publication Data
US 2010/0022017 A1  Jan. 28, 2010

(30) Foreign Application Priority Data

Sep. 1, 2005 (GB) .................................. 0517855.3
May 4, 2006 (GB) .................................. 0608839.7

(51) Int. Cl.
*C07K 14/00* (2006.01)
(52) U.S. Cl. ......... 530/350; 530/402; 530/409; 530/410
(58) Field of Classification Search .................. None
See application file for complete search history.

(56) References Cited

FOREIGN PATENT DOCUMENTS

| WO | 95/03429 | 2/1995 |
|---|---|---|
| WO | 2004/039487 | 5/2004 |
| WO | 2005/054855 | 6/2005 |

OTHER PUBLICATIONS

Okoh et al. A biosensor for inorganic phosphate using rhodamine-labeled phosphate binding protein. Biochemistry 2006, 45. 14764014771.*
Hirshburg et al. Crystal structure of phosphate binding protein labeled with a coumarin fluorphore, a probe for inorganic phosphate. Biochemistry 1998, 37, 10381-10385.*
International Search Report issued May 9, 2007 in the International (PCT) Application of which the present application is the U.S. National Stage.

* cited by examiner

*Primary Examiner* — Nashaat Nashed
(74) *Attorney, Agent, or Firm* — Wenderoth, Lind & Ponack, L.L.P.

(57) ABSTRACT

Binding of inorganic phosphate to a phosphate binding protein can result in changes to the stacking of appropriately positioned chromophores, thereby resulting in a detectable change. The invention provides a phosphate-binding protein that undergoes a conformational change from an initial conformation to a final conformation upon binding of phosphate, wherein the protein carries a first label and a second label, and wherein the first and second labels are arranged such that they exhibit molecular stacking that is perturbed on changing from one conformation to the other. Preferred labels are rhodamines.

12 Claims, 9 Drawing Sheets

5-IATR
$R^1 = ICH_2CONH, R^2 = H$

6-IATR
$R^1 = H, R^2 = ICH_2CONH$

Rhodamine B

R610 lactone

Rhodamine 123

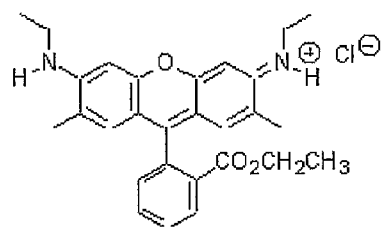

Rhodamine 6G

FIG. 7

```
Burkholderia       ------------------------------MS EPIMNFPGPDGAALDAMRNRLQR---  25
Bradyrhizobium     ---------------------------------------------MNP IYSRRRR----  10
Xylella            ---------------------------------------------MST ASQHLYK----  10
Myco.pstA-1        -----------------------------------MS PSTSIEALDQPVKPVVFRPLTL---  24
Azotobacter        VEAEEVPRARLAASGLPVDADGGEFMTRELLKVGNRELFGADFNWVVGEWLANPRKPESL  60
Bacteroides        ---------------------------------------------MEI LNNTKAK----  10
Salmonella         ---------------------------------------------MAA TKPAFNPPG-  12
Pasteurella        ---------------------------------------------MLR RKTQAETNR-  12
Myco.pstC-1.       ---------------------------------------------MLA RAGEVGRAGP  13
Myco.pstC-2        ------------------------------------------MV TEPLTKPALVAVDM  16
E.coli             -----------------------------MK VMRTTVATVVAATLSMSAFSVFAEA-  27
Erwinia            -----------------------------MT SMHKTLAQCVALTLSLSAVSALAAT-  27
Xanthomonas        ------------------MRRTPLPCNGVLRDVIPIATRSCSVISSIKSRLAVGVLAAAL  42
limicola           ------------MRCQLIMIFMFHTFNRYPIMMIKRFWKTAFMACAFAGLATGSAEAR-  46
Chromohalobacter   ------------------------MNR-----ILKTTALAAAVMSVAGVAQAQDETR-  28
phaeobacteroides   -------MTKTYSMTALLLMLAGFLSVVGCG- PKADQAAKDGQAASETEQTGEAIESAR-  51
Myco.pstA-2.       -----------------------------MG ESAESGSRQLPAMSPPRRSVAY---  24
Pseudomonas        ---------------------------------------------MSN ALLLLG----   9
Thermocellum       ---------------------------------------MKKMKRIVLTVTILALFITG---  20
```

FIG. 7(contd.)

```
Burkholderia       ----KRKAVNAIALTAS-----------------LGAMAFGLLWLVWILYT----TVHLG  60
Bradyrhizobium     ----KDIVVRGLCIAA-----------------AAFGVTWLALILIT----LLYNG  41
Xylella            ----RRRLINATAITIS----------------CIAALFGLFFLIWILWT----LISKG  45
Myco.pstA-1        ----RRRIKNSVATTFF----------------FTSFVVALIPLVWLLWV----VIARG  59
Azotobacter        VVFERREWGNFYGYLLGVKESGRLVAEGEGAWKELLSRIERVAGLHEQLAQ----LERAD 116
Bacteroides        ----RRSQGIAFGIFR-----------------LLS-LCIVLILFAILGF----IIYKG  43
Salmonella         ----KKG---DMIFSALV---------------KLAALIVLLMLGGIIVS----LIISS  45
Pasteurella        ----LNHHIIELLFRQTT---------------RFFAIFVFLLLAAVMTS----LVFGS  48
Myco.pstC-1.       AIRWLGGIGAVIPLLALV---------------LVLVVLVIEAMGAIRLNGLHFFTATE  57
Myco.pstC-2        RPARRGERLFKLAASAAG---------------STIVIAILLIAIFLLVR-----AVPS  55
E.coli             -------SLTGAGATFPAP--------------VYAKWADTYQKETGNKVN--YQGIGS  63
Erwinia            -------NLTGAGGTFPAP--------------VYNKWAAEYHTATGSQVN--YQGIGS  63
Xanthomonas        AMGAQAADVTGAGASFIYP--------------VMSKWSADYNTATKKQVN--YQSIGS  85
limicola           ------EQIRIVGSSTVFP--------------FASYVAEEFGKTTKFATP--VIESTG  83
Chromohalobacter   ------EQLRIVGSSTVYP--------------FASYVVEEFGATTDYPTP--VIESTG  65
phaeobacteroides   ------DYISVVGSSTVYP--------------FATVVAEQFGKTSDFKTP--KIESTG  88
Myco.pstA-2.       ----RRKIVDALWWAACVC--------------CLAVVITPTLWMLIG----VVSRA  59
Pseudomonas        ------------------------------LLAAVTASFAWLEIDFG-----ALFG  30
thermocellum       ------------------------------CATENNNEIVVVSRE---EGSGT  40

Burkholderia       VGGLS------------------------------------------------------  65
Bradyrhizobium     IAGLN------------------------------------------------------  46
Xylella            LPGIG------------------------------------------------------  50
Myco.pstA-1        WFAVTRS----------------------------------------------------  66
Azotobacter        IGRVNHALERLRLKERGLELGGDLDADAQADLAAERAQWGVRYRELESQLVVLQQEFNRD 176
Bacteroides        IGVIS------------------------------------------------------  48
Salmonella         WPSIQKFG---------------------------------------------------  53
Pasteurella        WDSFSTFG---------------------------------------------------  56
Myco.pstC-1.       WNPGNTYG---------------------------------------------------  65
Myco.pstC-2        LRANHANF---------------------------------------------------  63
E.coli             SGGVKQIIA--------------------------------------------------  72
Erwinia            SGGVKQIIA--------------------------------------------------  72
Xanthomonas        GGGIAQIKA--------------------------------------------------  94
limicola           SGGGHKLFG--------------------------------------------------  92
Chromohalobacter   SGGGLRLFC--------------------------------------------------  74
phaeobacteroides   SGGGFKLFA--------------------------------------------------  97
Myco.pstA-2.       VPVFH------------------------------------------------------  64
Pseudomonas        ADSLRQMG---------------------------------------------------  38
thermocellum       RGAFIELFG--------------------------------------------------  49
```

FIG. 7(contd.)

```
Burkholderia       ---------------------------------------LQ LFTESTPAPNTEGGGLAN  85
Bradyrhizobium     ---------------------------------------LE IFVADTPPPGSTEGGLRN  66
Xylella            ---------------------------------------LD LFTKITPPP-MQKGGLAN  69
Myco.pstA-1        ---------------------------------------GW WTHSLRGVLPEQFAGGVYH  87
Azotobacter        SVLVRTADGREEEITLGKVVRAYQPNAMGLGEKFGFYFAKLWEFVSDEPREANTEGGIFP 236
Bacteroides        ---------------------------------------WD FLTTAPTDGMTGGGIWP  67
Salmonella         ---------------------------------------FS FLWTKEWDAPNDIYGALV 73
Pasteurella        ---------------------------------------FS FLWHNDWNPVQESYGAII 76
Myco.pstC-1.       ---------------------------------------ET VVTDGVAHPVGAYYGALP 85
Myco.pstC-2        ---------------------------------------FT STQFDTSDDEQLAFGVRD 83
E.coli             ---------------------------------------NT VDFGASDAPLSDEKLAQEG 93
Erwinia            ---------------------------------------KT ADFGASDAPMKDEDLAKNG 93
Xanthomonas        ---------------------------------------AS VDFGSSDAPLKPEELAAAG 115
limicola           ---------------------------------------EG DGLATPDITNSSRRMKKSE 113
Chromohalobacter   ---------------------------------------NG VGLDTPDITNASRRMKPSE 95
phaeobacteroides   ---------------------------------------AG VGVEHPDITNASRRIKKSE 118
Myco.pstA-2.       ----------------------------------------WS VLVQDSQGNGGGLRN  81
Pseudomonas        ----------------------------------------DYASGFLSPDFSPAHLLA  56
thermocellum       ----------------------------------------IE EKDSNGNKVDKTTDEAT  68

Burkholderia       AIVGSLLLCGFGTLVGTPIGILAGVYLAEYGQKNLLASTIRFINDILLSAPS-------- 137
Bradyrhizobium     AIVGSIIMTVLGVGIGAPLGLFAGTYLAEYGRNDRLTSVIRFINDILLSAPS-------- 118
Xylella            AFFGSAIMCLLAIVIGTPLGIAAGTWLAEYGNTSKTSAVVRFVNDILLSAPS-------- 121
Myco.pstA-1        ALYGTLVQAGVAAVLAVPLGLMTAVYLVEYG-TGRMSRVTTFTVDVLAGVPS-------- 138
Azotobacter        AIFGTVMMTLIMAVLVTPFGVLAAIYLREYAKQGPLTRVIRIAVNNLAGVPA-------- 288
Bacteroides        AIVGTFYLMVGSALFAFPVGVMSGIYMNEYAPKGKLVRFIRVMTNNLSGIPS-------- 119
Salmonella         PIYGTLVTSFIALLIAVPVSFGIALFLTELA-PGWLKRPLGIAIELLAAIPS-------- 124
Pasteurella        PIVGTLITSFLALIIAVPISFGIAIFLTELA-PEWLRRPVGTAIEMLAAIPS-------- 127
Myco.pstC-1.       LIVGTLATSAIALIIAVPVSVGAALVIVERL-PKRLAEAVGIVLELLAGIPS-------- 136
Myco.pstC-2        LFMVTALSSITALVLAVPVAVGIAVFLTHYA-PRRLSRPFGAMVDLLAAVPS-------- 134
E.coli             LFQFPTVIGGVVLAVNIPGLKSGELVLDGKTLGDIYLGKIKKWDDEAIAKLN------PG 147
Erwinia            LFQFPTVIGGVVLAVNIPGIKSGELTLDGKTVGDIYLGTVKKWNDPAITKLN------PG 147
Xanthomonas        LAQFPSVIGGVVPVINVPGIAAGAVKLDGKTLGDIFLGKVTTWNDAAIVALN------PG 169
limicola           FERAQ--QNGVKTIHEAVIGYDGIVVANAKAAPALKLSRKDIFMALAEEVP----VKGQL 167
Chromohalobacter   FERCQ--ENGVTDITEAKIGYDGIAFAESNTNEPVNFTREQLFLALAAKVP----QDGEL 149
phaeobacteroides   CEMCA--ENGVSEVVELKIGYDGIVMANSKKAEPFKVSRKDIFLALAKEVPDPNGEDGTL 176
Myco.pstA-2.       AIIGTAVLAIGVILVGGTVSVLTGIYLSEFA-TGKTRSILRGAYEVLSGIPS-------- 132
Pseudomonas        IGRGALETLAMSAIGTLLAALLG--LLLALPASGRCGLPANAAARLLLNALR-------- 106
thermocellum       VVNSTSVVMTTVAGNKNSIGYISLGSLNDTVKAVKVDGVEPTVENIKNNTYK-------- 120
```

FIG. 7(contd.)

```
Burkholderia       IVIGLFVYAIVVAKSG--------------------------RFSGWAGVIALALLQIPI 171
Bradyrhizobium     IIIGLFIYGAVVVPMR--------------------------GFSAIAGSLALAVIVIPV 152
Xylella            IVLGLFVYTLYVMHTGG-------------------------HFSAFSGALALVFIVLPI 156
Myco.pstA-1        IVAALFVFSLWIATLGF-------------------------QQSAFAVALALVLLMLPV 173
Azotobacter        IVYGVFGLGFFVYVLGGSIDRLLFAEA--------LPAPTFGTPGLLWASLTLAILAVPV 340
Bacteroides        IVFGLFGMALFVNYMD----------------------FGDS-ILAGSLTLGLLCVPL 154
Salmonella         IVYGMWGLFIFAPLFATYFQEPVGNILSNIPFVGALFSGPAFGIGILAAGVILAIMIIPY 184
Pasteurella        IIYGMWGLFIFVPLFQEHIQPSLIEWFGDLPVFSYLFSGAPFGIGLFTAGLVLAIMIIPF 187
Myco.pstC-1.       VVVGLWGAMTFGPFIAHHIAPVIAHNAPDVPVLNYLRGDPGNGEGMLVSGLVLAVMVVPI 196
Myco.pstC-2        IIFGLWGIFVLAPKLEP-IARFLNRNLGWLFLFKQGNVSLAGGGTIFTAGIVLSVMILPI 193
E.coli             LKLPSQNIAVVRRADGSGTSFVFTSYLAKVNEEWKNNVGTGSTVKWPIGLGGKGNDGIAA 207
Erwinia            VKLPDANINVVRRADGSGTSFVFTSYLSKVNKDWSSKVGKGSTVNWPVGLGGKGNDGVAA 207
Xanthomonas        VKLPDSKITVVHRSDGSGTSFNFTNYLSKVNPDWKSKVGEGTAVQWPTGIGGKGNEGVAA 229
limicola           VKNPYKMWNQINPALPKQKILVYGPPTSSGTRDAFDEMVMEAASKKMTEYGTAAGK---- 223
Chromohalobacter   VDNPYTKWSDIDSSLPDREIMVYGPPTTSGTRDAFEELVMEAASEEMDAYGGEG------ 203
phaeobacteroides   VANPYTTWKEVNPELPEVKIEVLGPPPTSGTRDAFVELAMEAGAKEFAWIKALKKEDKDK 236
Myco.pstA-2.       IVLGYVGYLALVVYFD--------------------------WGFSLAAGVLVLSVMSIPY 167
Pseudomonas        AIPELVWAALMVLAAG--------------------------LGPNAGTLALALHTAGV 139
thermocellum       VFRPFIIATKENPGELT-------------------------QDFISFILSSDGQKVV 153

Burkholderia       VIRTTENMLKLVPNALREAAVALGTPKWRMVLKITLRASVGGIVTGVLLAVARIAGETAP 231
Bradyrhizobium     VLRTTEDMLLLVPNALREAASALGLPRSLVIKRIAYRAARSGLITGVLLATARVAGETAP 212
Xylella            VVRTTDEMLRLVPGQMREAALSLGIPQWKMIIQVLYRSASAGILTGILLALARISGETAP 216
Myco.pstA-1        VVRAGEEMLRLVPDELREASYALGVPKWKTIVRIVAPIAMPGIVSGILLSIARVVGETAP 233
Azotobacter        VIVATEEGLARIPRALREGSLALGATKAETLWKVVLPMASPAMMTGLILAVARAAGEVAP 400
Bacteroides        VIRTTEEALKAIPDSMREGSRALGATKLQTIWHVILPMGMPNIITGLILALGRVSGETAP 214
Salmonella         IAAVMRDVFEQTPVMMKESAYGIGCTTWEVIWRIVLPFTKNGVIGGIMLGLGRALGETMA 244
Pasteurella        IAAVMRDVFTIVPAILKESAYGLGSTTWEVMWKVVLPYTKTGVVGGIMLGLGRALGETMA 247
Myco.pstC-1.       IATTTHDLFRQVPVLPREGAIALGMSNWECVRRVTLPWVSSGIVGAVVLGLGRALGETMA 256
Myco.pstC-2        VTSISREVFRQTPLIQIEAALALGATKWEVVRMTVLPYGRSGVVAASMLGLGRALGETVA 253
E.coli             FVQRLPGAIGYVEYAYAKQNNLAYTKLISADGKPVSPTEENFACAAKGADWSKT--FAQD 265
Erwinia            FVQRLPGSVGYVEYAYAKQNSLAYTKLVDADGKAIAPSEKSFSDAAKGADWSTS--FAQD 265
Xanthomonas        YVKQIKGGIGYVELSYALQNKMAYTAMKNAAGKFVQPSDETFAAAANSADWGSSKDFYLV 289
limicola           ----YKKIRQDGVYVPSGENDNLIVQRIVKDRNAVGVFGYSFLEENADRIKGATVDGVAP 279
Chromohalobacter   ----YTDIRQDGPYVDAGENDNLIVQRLQENTTAFGIFGYSFLEENADSLTAASIDGVEP 259
phaeobacteroides   FKQISHTVREDGAYVEAGENDNLIVQKLDANPDALGVFGFSFLDQNKDKVQGSFVDGVEP 296
Myco.pstA-2.       IAKATESALAQVPTSYREAAEALGLPAGWALRKIVLKTAMPGIVTGMLVALALAIGETAP 227
Pseudomonas        LGRLFAEALENIPGEPAEAVRLAGGGRVAAFCYGTLPGVWPQLLAYTLYRWENNIRMASV 199
thermocellum       EENSYIAASEKGPYSSTKPSGKIVIAGSSSVTPLMEKLKEAYLKVNTNAEIEIQASDSTT 213
```

FIG. 7(contd.)

```
Burkholderia       LLFTALSNQFFSWDMSQP---------MANLPVTIYKFAMSP--FAEWQSLAWAGVFLIT 280
Bradyrhizobium     LLFTALSNQFFSLGLNKT---------MANLPVTINNFVQSP--YAYWKQLAWSGALLIT 261
Xylella            LLFTAFGNQYWSSNIFQP---------IASLPLVMNQFASSP--YKSWQLLAWSGALVLT 265
Myco.pstA-1        VLVLVGYSHSINLDVFHGN--------MASLPLLIYTELTNP--EHAGFLRVWGAALTLI 283
Azotobacter        LMLVGVVKLAPSLPVDGNYPYLHLDQKIMHLGFHIYDVGFQSPNVEAARPLVYATALLLV 460
Bacteroides        ILFTCAAYFLPQLPTS-------ILDQCMALPYHLYVISTSGTDMEAQLPLAYGTALVLI 267
Salmonella         VTFIIGNTYQLDSASLYMP------GNSITSALANEFAEAES---GLHVAALMELGLILF 295
Pasteurella        VTFVIGNAFHLP-ESLFSP------STSIASAIANEFNEAS----GLQKSALMELGLILF 296
Myco.pstC-1.       VAMVSGAVLGAMPANIYAT------MTTIAATIVSQLDSAMTDSTNFAVKTLAEVGLVLM 310
Myco.pstC-2        VLVILRSAARPGTWSLFDG------GYTFASKIASAASEFSEP---LPTGAYISAGFALF 304
E.coli             LTNQKGEDAWPITSTTFILIH--KDQKKPE-QGTEVLKFFDWAYKTGA-KQANDLDYASL 321
Erwinia            LTFQKGDNAWPITSTTFILVH--KEQANTA-KGAAVLQFFDWAYKNGG-KTTSALDYASL 321
Xanthomonas        MTNAAGDNAWPITATNFILVQ--KKPKNPA-GLKNTLEFFRWVYSKGD-AQAKALDYVPL 345
limicola           LPANITTGKYPVSRDLFFYVK--GSHLAQVKGLKEYVDLFLGEKMIGDYGYLKKIGLIPL 337
Chromohalobacter   EPEAISSGEYPVSRSLFFYVK--NQHADSVPAMYPYVDLFMSEQMISPMGYLKGLGLIPL 317
phaeobacteroides   AFSAIADGSYPLSRPLYFYVK--KAHVGTIPGMQEYLTEFTSEKAWGDEGYLTEKGLIPM 354
Myco.pstA-2.       LLYTAGWSNSPPTGQLTDS-------PVGYLTYPIWTFYNQP--SKSAQDLSYDAALLLI 278
Pseudomonas        LGFVGAGGLGQMLYLSLS--------------------------LFQEAQAATVILAML 232
thermocellum       GMKLAMEGTCDIGMASRELKE-------------SELKKLKPTVIAMDGLVVIVNKENPV 260

Burkholderia       LGVLGLNVLARSIFSKK----------- 297    <SEQ ID NO: 5>
Bradyrhizobium     ITVLALNIGARILGAERTAK-------- 281    <SEQ ID NO: 6>
Xylella            VFVLLVSLGARTLLLRNKIPNE------ 287    <SEQ ID NO: 7>
Myco.pstA-1        IVVATINLAAAMIRFVATRRR------- 304    <SEQ ID NO: 8>
Azotobacter        LVIALLNLSAVYIRNRLREKYKALDH-- 486    <SEQ ID NO: 9>
Bacteroides        VIILLVNLLANALRKYFEKKVKMN---- 291    <SEQ ID NO: 10>
Salmonella         VITFIVLAASKFMIMRLAKNEGAR---- 319    <SEQ ID NO: 11>
Pasteurella        LITTVVLSISRLLIMRIEKKEGRK---- 320    <SEQ ID NO: 12>
Myco.pstC-1.       VITLLTNVAARGMVRRVSRTALPVGRGI 338    <SEQ ID NO: 13>
Myco.pstC-2        VLTFLVNAAARAIAGGKVNG-------- 324    <SEQ ID NO: 14>
E.coli             PDCVVEQVRAAWKTNIKDSSGKPLY--- 346    <SEQ ID NO: 15>
Erwinia            PAPVVEQIRAAWKSNVKDSSGKALY--- 346    <SEQ ID NO: 16>
Xanthomonas        PDTLVSQIEAYWAKTLPR---------- 363    <SEQ ID NO: 17>
limicola           PKAKRDAVRASWTAKKVLSAASLD---- 361    <SEQ ID NO: 18>
Chromohalobacter   PEDAREQARSDVENRESLELSDLK---- 341    <SEQ ID NO: 19>
phaeobacteroides   PKEEREKYANVAMELIAVSCDEL----- 377    <SEQ ID NO: 20>
Myco.pstA-2.       VFLLLLIFIGRLINWLSRRRWDV----- 301    <SEQ ID NO: 21>
Pseudomonas        SLVLGVDALSGWGRHRWVWN-------- 252    <SEQ ID NO: 22>
thermocellum       SNLTSDQIKGIFKGEITSWNEVAK---- 284    <SEQ ID NO: 23>
```

INORGANIC PHOSPHATE ASSAYS

This application is a U.S. national stage of International Application No. PCT/GB2006/003228 filed Aug. 31, 2006.

All documents cited herein are incorporated by reference in their entirety.

TECHNICAL FIELD

This invention relates to assays for inorganic phosphate, particularly the detection and quantification of inorganic phosphate in biological solutions. More particularly, the present invention relates to a modified phosphate binding protein, and to the use of such a protein in a phosphate assay.

BACKGROUND ART

Inorganic phosphate (Pi) is involved in a large number of biological processes and it is desirable to be able to measure the concentration of Pi and the changes in such concentration in biological systems. Phosphate assays, which measure Pi concentration, are useful in a number of diagnostic methods, as well as in research into the functioning of biological systems.

Enzymatic phosphate assays are based on a phosphate-requiring enzyme, often a phosphorylase. Reference 1 describes a method in which a purine-nucleoside phosphorylase is used to convert a nucleoside (inosine) to ribose-1-phosphate and a base, in this case, hypoxanthine. The hypoxanthine is then converted into a coloured agent, from which the extent of inosine conversion, which is dependent upon Pi concentration, may be determined.

Enzymatic phosphate assays tend to be relatively insensitive. For example, reference 2 describes a method that may not be used below Pi concentrations of 2 µM. Furthermore, although more rapid than chemical phosphate assays, enzymatic phosphate assays are generally too slow to allow the study of kinetics of many biological systems in real time.

A number of phosphate assay systems are known in the art. For example, Malachite Green Phosphate Detection (MGPD) kits are useful for the quantitative detection of Pi. The Quantichrom Phosphate Assay Kit (BioAssay Systems) is one such MGPD kit. However, the assay used is very slow requiring incubation to achieve colour development. Furthermore, MGPD kits are generally useful only at high concentrations of phosphate (approximately 0.3 mM-50 mM).

The EnzChek Phosphate Assay Kit from Invitrogen (Molecular Probes) has a phosphate concentration detection range of 2 µM-150 µM and a workable pH range of 6.5-8.5 (taken from data sheet). Again, this test is unsuitable for the detection of low phosphate concentration.

A number of proteins are known which specifically bind to Pi. For example, transport of Pi into and out of cells and organelles is executed by specific transport proteins. In bacterial cells, this is achieved by way of a high affinity transport system dependent on a phosphate-binding protein. Such proteins are able to specifically recognise inorganic phosphate, bind to it and transport it across cell membranes or between cellular compartments.

An example of such a protein is the *E. coli* phosphate binding protein (PBP) which is encoded by the phoS gene of *E. coli*. This protein is located in the periplasm of *E. coli* as part of the Pi scavenging system of the bacterium, which operates under conditions of Pi starvation, and its binding affinity for Pi is very high. The phoS gene has been cloned and sequenced [3,4]. Moreover, it has been determined that PBP binds Pi tightly, and the crystal structure of the Pi-bound form has been solved to high resolution [5], as has the structure of a Pi-free form [6]. These studies have shown PBP to be a monomeric protein of 35 kD separated into two domains, with a Pi-binding cleft between them. The Pi-binding cleft moves between open and closed positions on Pi binding.

Reference 7 describes the modification of PBP to introduce a coumarin label at the edge of the Pi-binding cleft. The conformational change to the binding cleft which occurs upon phosphate binding is translated into an increase in the fluorescence of the coumarin label. However, the universality of phosphate in biological systems and the desire to monitor the kinetics of biological and chemical processes which involve the consumption or production of Pi makes the development of further and improved phosphate assays important.

DISCLOSURE OF THE INVENTION

The invention is based on the discovery that, by attaching multiple labels to PBP, improvements in the detectable changes that occur upon Pi binding can be achieved. Fluorophores such as rhodamines can stack, either with themselves (in which case the stacking is referred to as dimerisation) or with another aromatic molecule, to form a complex with different optical properties from those of the non-stacked molecules. It has been found that Pi binding to PBP can result in changes to the stacking of appropriately positioned chromophores, thereby resulting in a detectable change. Moreover, it has surprisingly been found that labels attached to regions of PBP that are remote from the Pi binding cleft can still give detectable changes when Pi binds to the protein, thereby allowing labels to be attached with minimal interference to Pi binding.

Thus the invention provides a phosphate-binding protein that undergoes a conformational change from an initial conformation to a final conformation upon binding of phosphate, wherein the protein carries a first label and a second label, and wherein the first and second labels are arranged such that they can exhibit molecular stacking. This stacking is altered by the conformation change on binding Pi. The alteration in stacking results in a detectable change, indicating a change in Pi binding status.

Preferably the change is such that the first and second labels can exhibit molecular stacking either (a) in the initial conformation but not in the final conformation, or (b) in the final conformation but not in the initial conformation.

The use of two labels contrasts with reference 28, which specifically teaches that multiple site labelling should be avoided when attaching fluorophores to PBPs. Reference 25 also refers to double labelling as leading to a decrease in signal when using a single fluorophore.

The invention also provides a phosphate-binding protein that undergoes a conformational change from an initial conformation to a final conformation upon binding of phosphate, wherein phosphate binding occurs at a binding site, and wherein the protein carries a label that is attached to a region of the protein remote from the binding site. The label can give a first detectable signal in the initial conformation and a second detectable signal in the final conformation, wherein said first and second detectable signals are different from each other.

The invention also provides a phosphate-binding protein that undergoes a conformational change from an initial conformation to a final conformation upon binding of phosphate, wherein the protein carries a rhodamine label. The rhodamine label can give a first detectable signal in the initial conformation and a second detectable signal in the final conformation, wherein said first and second detectable signals are different from each other.

The invention also provides a phosphate-binding protein that undergoes a conformational change from an initial conformation to a final conformation upon binding of phosphate, wherein the protein carries one or more labels, and wherein the label(s) is/are attached via a non-chiral centre(s).

Compared to the coumarin-labelled PBPs of reference 7, the PBPs of the invention show a higher apparent binding capacity for Pi. In particular, they show a linear signal change up to the maximal binding capacity for Pi.

The Phosphate Binding Protein (PBP)

The invention utilises a 'phosphate binding protein', which is the name commonly given to the primary phosphate receptor of the ABC transport system found in bacteria, also known as the periplasmic phosphate binding receptor. PBPs are also present in eukaryotes [8]. PBPs are part of the active phosphate transfer system and reversibly bind and release Pi. They are members of the protein superfamily of extracellular solute-binding receptors [9] and consist of two domains linked by a hinge region [10]. The phosphate-binding site is located at the interface between the two domains. The proteins typically adopt two conformations: a phosphate-free open form and a phosphate-bound closed form, which interconvert via a hinge-bending mechanism upon phosphate binding. Native PBP is formed after cleavage of a precursor, and PBPs can be lipoproteins. The PBPs are robust to denaturation and bind to Pi specifically and tightly.

PBPs have been described for a number of bacteria and in mammals, and the invention can use any of these. A sequence alignment of a number of PBPs from different organisms is shown in FIG. 7. Any of these PBPs or similar PBPs may be used in the present invention.

The primary phosphate receptors of the gram-negative bacterial ABC transport system are Periplasmic Binding Proteins. Periplasmic Binding Proteins form one of the largest protein families in eubacterial and archaebacterial genomes and are considered to be derived from a common ancestor based on similarity of three-dimensional structure, mechanism of ligand binding and gene operon structure. Periplasmic Binding Proteins share common features of three-dimensional structure and patterns of ligand binding despite large length variation and low sequence identity. Periplasmic Binding Proteins consist of two globular domains of mainly α/β type. The ligand is bound in a cleft between the two domains and engulfed by both. A hinge-bending motion between the two domains is accompanied by ligand binding [10]. Preferably, the phosphate receptors used in the present invention have these three features.

The genes for the ABC transport system have also been discovered in bacteria without a periplasmic space, such as gram-positive *Mycobacteria* [11]. Primary phosphate receptors from *Mycobacteria* and other Gram-positive bacteria have a tether to anchor them to the membrane and have a similar function to the periplasmic primary phosphate receptors. The function of the similar protein(s) in mammals is unknown.

Periplasmic Binding Proteins are classified as type I or type II based in the topological arrangement of the central β-sheets in their core structure [12]. Preferably the PBPs of the present invention are Type II wherein the sheet topology of both protein domains takes the form $\beta_2\beta_1\beta_3\beta_n\beta_4$ where $\beta_n$ represents the strand just after the first crossover from the N-terminal domain to the C-terminal domain, and vice versa.

The invention can also use precursors, mutants, and variants of these PBPs, provided that the essential function of phosphate binding is retained with its associated conformation change. Mutant PBPs that retain phosphate binding have been described in the art, and these mutants can be used with the invention, For the *E. coli* protein (SEQ ID NO: 1), for instance: reference 13 discloses a mutant PBP with Asp-137 replaces by And, Gly or Thr, with little effect on phosphate affinity; references 14 & 15 disclose a Thr-141-Asp mutant, with the aim of changing phosphate affinity; references 7, 27, 28 & 29 disclose a Ala-197-Cys mutant of the *E. coli* PBP (SEQ ID No:1); reference 16 discloses a Ala-197-Trp mutant; reference 14 discloses an Asp-56-Asn mutant, etc. The use of mutants is preferred, as attachment of labels to the protein will frequently require a suitable amino acid residue (e.g. a Cys residue) to be introduced at a desired position.

Because of their role in phosphate uptake, expression of PBPs is repressed by Pi under normal conditions, but is induced under conditions of Pi limitation. Thus PBP is sometimes referred to as 'the phosphate-repressible phosphate-binding protein'. Its gene nomenclature is typically PstS (from 'Pi-Specific Transport') or PhoS, but the protein has also been referred to as nmpA, phoR2, R2pho and phoR2a. In *Mycobacterium tuberculosis* the protein has been referred to as 'protein antigen B' (PAB).

Native PBPs bind to both monobasic and dibasic Pi, but mutagenesis can be used to give specificity. For instance, reference 15 describes how the *E. coli* sequence was mutated at the ligand-binding site in order to restrict binding to only the monobasic ion.

A particularly preferred protein for use with the invention is the *E. coli* PhoS protein (SEQ ID NO: 1), because it has been extensively studied. The sequence of native *E. coli* PhoS is as follows (PDB accession P06128; SEQ ID NO: 1 herein):

MKVMRTTVATVVAATLSMSAFSVFAEASLTGAGATFPAPVYAKWADTYQK

ETGNKVNYQGIGSSGGVKQIIANTVDFGASDAPLSDEKLAQEGLFQFPTV

IGGVVLAVNIPGLKSGELVLDGKTLGDIYLGKIKKWDDEAIAKLNPGLKL

PSQNIAVVRRADGSGTSFVFTSYLALKVNEEWKNNVGTGSTVKWPIGLGG

KGNDGIAAFVQRLPGAIGYVEYAYAKQNNLAYTKLISADGKPVSPTEENF

ANAAKGADWSKTFAQDLTNQKGEDAWPITSTTFILIHKDQKKPEQGTEVL

KFFDWAYKTGAKQANDLDYASLPDSVVEQVRAAWKTNIKDSSGKPLY

This 346-mer is a precursor for the mature protein, which is formed by cleavage of the N-terminal 25 residues (underlined). The invention preferably uses a mature protein.

For the covalent attachment of labels, one form of *E. coli* PhoS is as follows, in which Asn 226 and Ser 299 have been mutated to Cys (SEQ ID NO: 2):

EASLTGAGATFPAPVYAKWADTYQKETGNKVNYQGIGSSGGVKQIIANTV

DFGASDAPLSDEKLAQEGLFQFPTVIGGVVLAVNIPGLKSGELVLDGKTL

GDIYLGKIKKWDDEAIAKLNPGLKLPSQNIAVVRRADGSGTSFVFTSYLA

KVNEEWKNNVGTGSTVKWPIGLGGKGNDGIAAFVQRLPGAIGYVEYAYAK

QNNLAYTKLISADGKPVSPTEENFA<u>C</u>AAKGADWSKTFAQDLTNQKGEDAW

PITSTTFILIHKDQKKPEQGTEVLKFFDWAYKTGAKQANDLDYASLPD<u>C</u>V

VEQVRAAWKTNIKDSSGKPLY

Additionally, for the covalent attachment of labels, one form of *E. coli* PhoS is as follows, in which Ala 17 and Ala 197 have been mutated to Cys (SEQ ID NO: 3):

```
EASLTGAGATFPAPVYCKWADTYQKETGNKVNYQGIGSSGGVKQIIANTV

DFGASDAPLSDEKLAQEGLFQFPTVIGGVVLAVNIPGLKSGELVLDGKTL

GDIYLGKIKKWDDEAIAKLNPGLKLPSQNIAVVRRADGSGTSFVFTSYLA

KVNEEWKNNVGTGSTVKWPIGLGGKGNDGIAAFVQRLPGAIGYVEYCYAK

QNNLAYTKLISADGKPVSPTEENFANAAKGADWSKTFAQDLTNQKGEDAW

PITSTTFILIHKDQKKPEQGTEVLKFFDWAYKTGAKQANDLDYASLPDSV

VEQVRAAWKTNIKDSSGKPLY
```

Additionally, for the covalent attachment of labels, a form of *E. coli* PhoS is as follows, in which Lys-229 and Glu-302 have been mutated to Cys (SEQ ID NO: 4):

```
EASLTGAGATFPAPVYAKWADTYQKETGNKVNYQGIGSSGGVKQIIANTV

DFGASDAPLSDEKLAQEGLFQFPTVIGGVVLAVNIPGLKSGELVLDGKTL

GDIYLGKIKKWDDEAIAKLNPGLKLPSQNIAVVRRADGSGTSFVFTSYLA

KVNEEWKNNVGTGSTVKWPIGLGGKGNDGIAAFVQRLPGAIGYVEYAYAK

QNNLAYTKLISADGKPVSPTEENFANAACGADWSKTFAQDLTNQKGEDAW

PITSTTFILIHKDQKKPEQGTEVLKFFDWAYKTGAKQANDLDYASLPDSV

VCQVRAAWKTNIKDSSGKPLY
```

Labels

The PBPs of the invention carry labels. Preferred labels are those that can exhibit molecular π-π stacking, which will thus include aromatic rings. These include the rhodamine labels.

Dye stacking is a non-covalent interaction between two chromophores having planar aromatic rings, and it occurs when the rings are separated by a distance that is short enough to allow them to interact e.g. to form dimers or trimers. The detectable signal of the stacked molecules is different from that of the unstacked molecules (e.g. stacking can cause quenching of signals, and so stacked chromophores will typically show a decreased fluorescence signal intensity relative to the individual unstacked chromophores), and this difference can be used to detect the presence or absence of stacking. Stacked chromophores can have absorption spectra with (i) a characteristic decrease in the principal absorption peak as chromophore concentration increases and (ii) a characteristic shoulder peak ('band splitting' [17]).

For example, rhodamine chromophores can form dimers at high concentrations in solution [18,19]. The dimer ($\lambda_{max}$ ~520 nm) has a different absorbance spectrum from the monomer ($\lambda_{max}$ ~550 nm), and has little or no fluorescence in comparison with the monomer [20,21]. The inventors have found that this optical difference between free monomer and dimer in solution can be retained when two labels interact when attached to a protein. Two rhodamine chromophores attached to suitable positions in the protein can form dimers, whose interaction is altered when ligand binds to the protein. The invention can spectroscopically detect the difference between the Pi-free and Pi-bound conformations of PBP. Typical spectral changes using a pair of rhodamine labels covalently attached at positions 17 and 197 of a mutant PBP are shown in FIG. 1 (absorption) and FIG. 2 (emission). References 21, 22 and 23 give further examples of fluorescence changes caused by alteration of molecular stacking of rhodamines attached to biomolecules. The stacking interaction utilised by the invention is different from the phenomenon known as FRET (Fluorescence Resonance Energy Transfer). In FRET, emission from a first chromophore (donor) is used to excite a second chromophore (acceptor) in close proximity through space, thereby resulting in a change in properties depending on the distance and relative orientation between the two chromophores. Molecular stacking takes place through the physical interaction of ground states of the two moieties, whereas fluorescence quenching occurs through a phenomenon called exciton coupling [24].

Labels that can undergo molecular stacking are well known in the art. Stacking can occur between identical chromophores, and can also occur between different chromophores.

Labels used with the invention can give various signals, but preferred labels are luminescent labels. Luminescent labels include both fluorescent labels and phosphorescent labels. However, the use of other labels is envisaged. For example, electrochemical labels could be used wherein alteration in the environment of the labels will give rise to a change in redox state. Such a change may be detected using an electrode.

The use of fluorescent labels, which may be excited to fluoresce upon exposure to certain wavelengths of light, is preferred. The fluorescent label can be selected from the group consisting of rhodamines, cyanines, pyrenes and derivatives thereof.

Preferred fluorescent labels are based on a xanthene nucleus, which can readily undergo π-π sacking to form dimers:

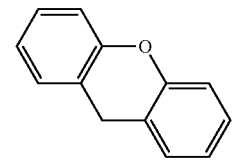

Such labels include the rhodamine fluorophores, which include the following core structure:

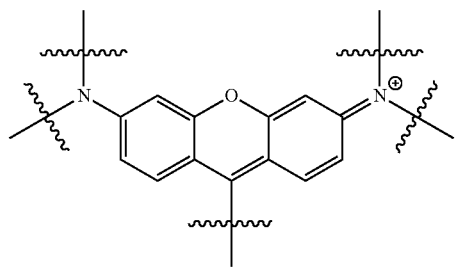

In addition to the xanthene and the two amino groups, the rhodamine core generally includes a further aromatic ring with a carboxylic substitution, as shown below:

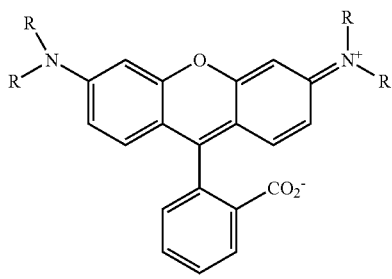

Examples of specific rhodamine fluorophores that can be used with the invention are shown in FIG. 6. Preferred rhodamine labels are functionalised to give high selectivity for reaction with thiols, such as the haloacetamidotetramethylrhodamine (XATR) molecules, even more preferably iodoacetamidotetramethylrhodamine (IATR) and bromoacetamidotetramethylrhodamine (BATR) molecules. The most preferred labels are 5-IATR and 6-IATR, shown in FIG. 6.

Where labels can have different isomers, it is preferred to use a single isomer. Thus, for example, where a rhodamine label is capable of existing as different structural isomers (e.g. 5-IATR and 6-IATR), the invention preferably uses a single isomer in a single PBP.

Where two labels are attached to a single PBP, the magnitude of the detectable change seen on Pi binding is preferably greater than the magnitude of the detectable change seen on Pi binding to a PBP with either of the two labels attached without the other being present.

The use of two stackable labels to detect a conformational change in a protein is not restricted to PBPs. For instance, the labels can be used with any periplasmic binding proteins, including those that bind leucine, isoleucine, valine, L-arabinose, glucose, galactose, D-ribose, lactose, purine, histidine, lysine, arginine, ornithine, glutamine, spermidine, putrescine, maltose, D-maltodextrin or sulphate. Thus, the invention more generally provides a protein that undergoes a conformational change from an initial conformation to a final conformation upon binding of a ligand, wherein the protein carries a first label and a second label, and wherein the first and second labels are arranged such that they exhibit molecular stacking that is altered by the change in conformation. The protein preferably has a single polypeptide chain and is not subject to enzymatic cleavage. A multi-subunit protein can also be used with the invention, providing that the subunits remain associated through the conformation change. The protein is preferably a periplasmic binding protein, as described above.

The Conformational Change

On binding to phosphate, PBPs undergo a conformational change [5, 6, 25]. The cleft containing the Pi binding site closes, causing a change in the relative distance and/or orientation of the protein's two globular domains. These alterations in structure, from an initial conformation to a final conformation, are exploited in the methods of the invention.

The invention preferably exploits the conformational change by attaching labels such that their separation distance increases or decreases, or such that they rotate relative to each other. Where two labels are attached, the movement can be used to change their ability to exhibit molecular stacking, as described above. Thus the orientation of the first and second labels changes between the initial conformation and the final conformation, and preferably their separation increases.

When Pi binds to the PBP, the movement of labels can cause stacking to occur, or can disrupt stacking that is present in the Pi-free PBP. In a third option, one stacking interaction is replaced with a different stacking interaction (e.g. using three labels, or using two labels and a stacking interaction with an aromatic amino acid in the PBP). The preferred option is where stacking is lost on Pi-binding, such that fluorescence quenching (e.g. by dimerisation) is decreased relative to the Pi-free protein. Accordingly, Pi-binding to the PBP will cause a increase in label-derived fluorescence.

Attachment of Labels

The PBPs of the invention have labels attached to them. The covalent attachment of extrinsic labels to proteins is well known (e.g. see chapter 8 of reference 26).

Different cysteine residues show different reactivities to labelling reagents, which can be assessed using DTNB (5,5'-dithio-bis(2-nitrobenzoic acid) [25]). For PBPs, reactivity can also be affected by the presence of bound Pi, In such cases, a phosphate mop (see below) can be used during labelling, to ensure that protein is in a Pi-free conformation.

Labels can be attached via amines or carboxyl residues on amino acid side chains, but it is preferred to use covalent linkage via thiol groups on a cysteine residue. Where more than one label is attached to a protein, these are preferably attached to separate amino acid residues.

If appropriate, a natural cysteine residue in the PBP can be used for attachment of the label. As the *E. coli* Phos protein (SEQ ID NO: 1) does not include any cysteine residues, these must be artificially introduced e.g. by site-directed or random mutagenesis. The introduction of a single cysteine at different positions into SEQ ID NO:1 has previously been described e.g. in reference 7, 25 and 27-29.

Where a cysteine residue has to be introduced, either by insertion or substitution, a number of factors should be considered. For instance, Pi-binding in the *E. coli* Phos (SEQ ID NO: 1) involves amino acids 10, 11, 38, 56, 137, 139 and 140 (see FIG. 3 of ref. 15). Mutagenesis should avoid these critical residues. It should also avoid the introduction of side chains that will interfere with access to the binding cleft. It should also avoid residues where an attached label will interfere with the binding cleft. Moving away from the Pi-binding site, however, specific individuals residues become less critical to the integrity and activity if PBP. The crystal structures 1A40, 11XG, 11XH, 11XI, 10IB, 1PBP, 1QUI, 1QUJ, 1QUK, 1QUL and 2ABH), including a structure including a covalently-attached fluorescent label [29], and these can be used to locate residues in suitable locations within the 3D structure of the protein. For a PBP where no crystal structure is available, homology modelling and alignment with the known prior art sequences can be used to identify residues for mutagenesis. The inventors have found that the best locations for mutation are those in regions of secondary structure rigidity, such as helical regions, particularly for *E. coli* PhoS (SEQ ID NO: 1).

The alignment shown in 7 shows that PBPs from different organisms display both conserved and non-conserved amino acids. The FIG. 7 alignment, and others alignments created using further PBPs, can be used to identify candidate amino acid residues for mutagenesis. Residues which are less conserved between proteins are more likely to tolerate mutation.

Where more than one cysteine residue is to be introduced, the same criteria apply. If attached chromophores are to interact, however, the residues must be selected such that (a) they are in proximity to each other, and (b) the conformational change that occurs on Pi-binding affects one or both of the residues to cause a change in position or orientation or electronic environment of a label attached thereto. Amino acids that move apart on Pi-binding are potential sites for label attachment. The residues may be close to each other in the PBP's primary sequence, or may be far away, but the available 3D structures can be used to determine the spatial proximity of chromophores (which will also have known structures) attached to any particular pair of amino acids, both before and after Pi-binding, enabling assessment of likely molecular stacking. Typically, the α-carbons on two residues chosen for label attachment will be separated by between 0.7-2.2 nm (e.g. 0.8-1.3 nm) in either the Pi-bound or Pi-free protein, and by a larger distance in the other form.

Preferably, residues chosen for label attachment are surface located. Such residues are more easily accessible for labelling purposes and are less likely to disrupt the tertiary structure of the protein when labelled.

Typical PBPs have two globular domains. Where two residues are chosen these may both be in the same globular domain, or there may be one per globular domain.

For example, PhoS crystal structure analysis shows that, as the cleft between the domains closes on phosphate binding, amino acids located on either side of the phosphate-binding cleft get closer in the Pi-bound structure than in the Pi-free structure. However, this movement is also transmitted to structural changes in other parts of the protein. The hinge consists of two extended pieces of the polypeptide, located centrally in the protein. On Pi-binding, the cleft closes on one side of the hinge to produce a rocking motion of the protein domains relative to each other, exposing a new 'cleft' on the opposite side of the protein.

In one embodiment of the invention, labels are attached to amino acid residues in a region of the protein remote from the binding site. Preferably, such amino acid residues are not involved in binding Pi (i.e. directly coordinate with Pi or indirectly via one other amino acid) or on the surface of the binding cleft. Additionally, or alternatively, labels are attached to amino acid residues on opposite sides of the binding cleft.

Using *E. coli* PhoS (SEQ ID NO: 1), eight preferred amino acid residues for substitution by cysteine are, numbered from the N-terminus of the mature phoS PBP [3]: Ala-17, Ala-197, Glu-222, Asn-226, Lys-229, Glu-247, Ser-299, Glu-302. Where a pair of cysteine residues is introduced, five preferred pairings are: 17 & 197, 229 & 302; 247 & 299; 222 & 299; 226 & 299. Ala-17 and Ala-197 are both mutated to cysteine residues (e.g. SEQ ID NO: 2).

Other possible attachment pairs include Glu-222 & Asp-298, Glu-62 & Lys-235, Asn-226 & Gly-230 and Lys-229 & Ser-299.

The corresponding amino acid residues in other PBPs can be identified based on sequence homology e.g. using the alignment of FIG. 7.

Fluorophores will rarely be attached to an amino acid directly, but will instead be attached via a linker. The choice of linker can also have an effect on the way the labelled PBP functions, as the size, shape and flexibility of the linker can change the ability of a linker to come into proximity with other groups. Haloacetamide linkers have been found to be useful.

Labels are preferably attached to the PBP in a manner that does not introduce a new chiral centre. Thus the label-protein adduct does not exist in diastereomeric form. This can be achieved by the use of linkers such as the haloacetamides (preferably iodoacetamides). When a maleimide, previously used to attach coumarin fluorophores [7], reacts with a cysteine, the resulting thio-substituted succinimide can exist as diastereoisomers that have different responses to Pi binding [25]. The use of a linker that does not introduce a new chiral centre thus allows a substantially homogenous labelled PBP to be obtained.

After attachment of the label, labelled protein will usually be purified to separate it from free label and from any mis-labelled protein. The mis-labelled protein may be unlabelled protein with which label did not react or protein where label has attached in the wrong position (either in place of or in addition to the desired label). During purification of the labelled protein, treatment with a thiol reagent may be included, such as β-mercaptoethanol, dithiothreitol or sodium 2-mercaptoethanesulfonate as this can improve the fluorescence response of the protein.

Where more than one label can be attached, it is preferred to use the protein in homogenous form. A homogenous form, e.g. pure double-labelled species, may be purified (e.g. by ion exchange and/or hydrophobic interaction chromatography) to obtain homogenous, double-labelled species. Single and double labelled PBPs can be distinguished by methods such as electrospray mass spectrometry.

Assay Methods

The labelled PBPs of the invention can be used in assays for detecting inorganic phosphate in a sample. These assays can be qualitative or quantitative. The invention is particularly useful for following the kinetics of reactions, because of the rapid reaction time of the PBPs. Preferably, the PBP is used for kinetic measurements in bulk solution, such as in stopped-flow applications. The assays can be for general biochemical use, or for diagnostic use e.g. for diagnosis of disease. For example, measurements of inorganic phosphate may be used in diagnosis of hyper vitaminosis D, hypoparathyroidism, renal failure, rickets and Fanconi syndrome, as well as for monitoring the causes and treatment of these diseases.

The labelled PBPs of the invention may also be useful for the identification and development of drugs against phosphate-associated diseases, such as those in which phosphatase inhibitors might be useful. For example, over-expression of the receptor-like human protein tyrosine 'phosphatase a' (PTPa) results in persistent activation of pp 60C-SRC with concomitant cell transformation and tumourigenesis. PTPa may function as an oncogene. Tumours such as human colon carcinoma exhibit an elevated level of pp60C-SRC kinase activity. Inhibitors of PTPa are therefore of use in the treatment of tumours. A high throughput screen assaying for Pi can be used for the identification of suitable lead compounds.

The sample may be from any source, including serum, urine, saliva, sweat, tissue culture, cell extracts, cell lines, food, beverages, pharmaceuticals and environmental (e.g. water). If concentrations of Pi in the sample are high, samples may be diluted as necessary to achieve accurate quantification of Pi levels.

These methods can be performed in vitro or in vivo, but will typically be in vitro assays.

Thus the invention provides a method for detecting inorganic phosphate in a sample, comprising the steps of: (i) mixing the sample with a PBP of the invention, and (ii) detecting a change in the mixture arising from interaction between the inorganic phosphate and the PBP. The change detected in step (ii) can be related to the concentration of inorganic phosphate in the sample.

The invention also provides a PBP of the invention, for use in an assay of inorganic phosphate.

An example assay would be to measure Pi release from actomyosin in demembranated muscle fibres or from helicases during translocation along DNA.

A "phosphate mop" [30] may used to reduce the background levels of phosphate. Preferably, the phosphate mop is an enzymatic system to remove the phosphate by chemical reaction. A 7-methyl guanosine (MEG) and purine nucleoside phosphorylase (PNPase) system is preferred.

The invention also provides a kit comprising a protein of the invention and a phosphate mop.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

Where two labels "exhibit molecular stacking", this typically means that their emission and/or excitation spectra are substantially identical to those of a stacked dimer.

BRIEF DESCRIPTION OF DRAWINGS

FIG. 7 shows a sequence alignment of PBPs from various organisms. The protein sequences shown are as follows:

Figure 1:
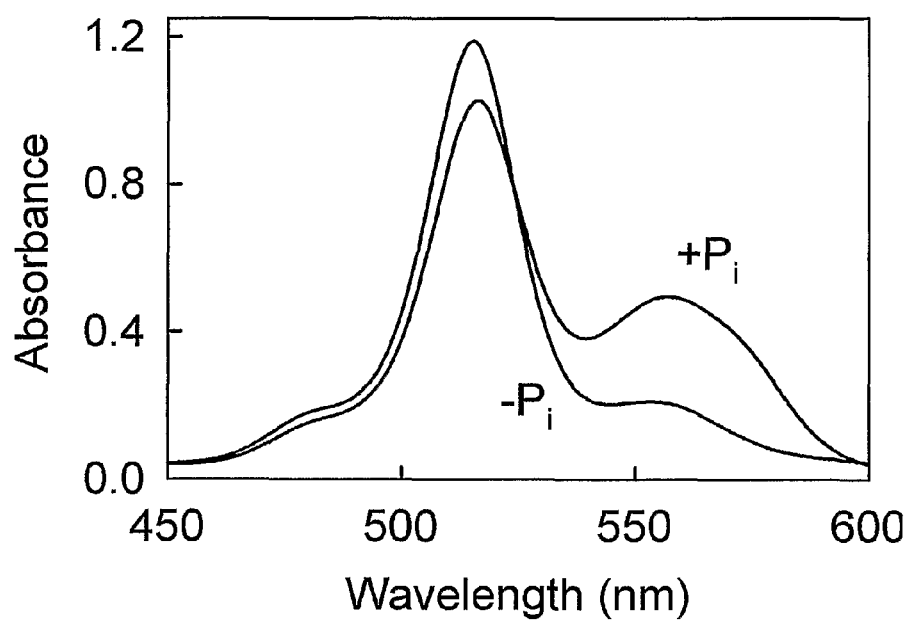
FIG. 1 shows the absorbance spectra of a preferred labelled protein of the invention (Ala17Cys/Ala197Cys mutant)

Myco.pstA-1; from *Mycobacterium tuberculosis* and its a membrane bound component of phosphate transport.

Myco.pstA-2; from *Mycobacterium tuberculosis* also a component of phosphate uptake.

Myco.pstC-1; phosphate ABC transporter from *Mycobacterium bovis*.

Myco.pstC-2; phosphate transporter from *Mycobacterium tuberculosis*.

phaeobacteroides; from *Chlorobium phaeobacteroides* BSI.

limicola; full name is *Chlorobium limicola* DSM 245 thermocellum; full name is *Clostridium thermocellum* ATCC 27405

Erwinia; full name is *Erwinia amylovora*

Chromohalobacter; full name is *Chromohalobacter salexigens* DSM 3043

Burkholderia; full name is *Burkholderia cenocepacia*

Azotobacter; full name is *Azotobacter vinelandii* AvOP

Xanthomonas; full name is *Xanthomonas campestris* pv. campestris str. 8004

Salmonella; full name is *Salmonella enterica* subsp. enterica serovar Choleraesuis str. SC-B67

Bradyrhizobium; full name is *Bradyrhizobium japonicum* USDA 110

Xylella; full name is *Xylella fastidiosa*

Bacteroides; full name is *Bacteroides fragilis*

Pseumonas; full name is *Pseudomonas aeruginosa*

Pasteurella; full name is *Pasteurella multocida*

MODES FOR CARRYING OUT THE INVENTION

Preparation of Mutant PBPs

In order to implement the labeling strategy, it was decided to introduce two thiols into E. coli PBP that could be readily labeled with rhodamines. That was most likely to be achieved with cysteines that are exposed at the surface. Furthermore, the cysteines should be sufficiently close so the rhodamines can interact with each other. The distance between them should change between the phosphate-bound and phosphate-free structures to enable there to be a possibility of a change in extent of interaction.

Wild-type *E. coli* PBP has no cysteine residues for covalent attachment of labels, so two thiols were introduced for labelling with rhodamine. For selecting a suitable pair of residues, two crystal structures of PBP were used: (a) MDCC-labelled PBP with bound Pi [29]; and (b) a mutant PBP with reduced affinity for Pi, which enabled a high resolution structure to be obtained of Pi-free PBP [6]. Examination of these structures enabled the choice of several pairs of amino acids on the surface, not apparently involved in side-chain interactions and with their α-carbons ~1 nm apart. In addition the distance between these pairs was different in the apo and Pi-bound structures.

Two different regions of the protein were examined. Firstly, as the Pi-binding cleft between PBP's globular domains closes on the binding of Pi, the two surface regions, located one either side of this cleft, get closer in the Pi-bound structure than in the Pi-free form. However, the surface movement is complex as the cleft closure is produced not only by hinge bending but also by a twisting of the domains relative to each other. This movement is also transmitted to structural changes in other parts of the protein. The hinge is formed by of two extended pieces of the polypeptide, located somewhat centrally in the protein. When the Pi-binding cleft closes on one side of the hinge, there is in essence a rocking motion of the domains relative to each other and a new, small "cleft" forms on the opposite side of the protein. This movement also gives amino acids suitable for label attachment.

Several pairs of mutation sites were identified, mainly remote from the binding cleft, which are not apparently involved in side-chain interactions and were approximately 1 nm apart. In addition, the separation of the residues' α-carbons changed between the Pi-bound and Pi-free crystal structures and these distances are given for each pair (numbered from the N-terminus of the mature phoS PBP):

(a) Lys-229 and Glu-302 (1.2 and 1.7 nm).
(b) Glu-247 and Ser-299 (1.6 and 2.2 nm).
(c) Asn-226 and Ser-299 (1.1 and 1.6 nm).
(d) Glu-222 and Ser-299 (1.5 and 1.8 nm).

In addition, Ala-17 and Ala-197 (1.6 and 1.3 nm) mutant was identified as suitable to study. These mutations may monitor the movement at the binding cleft, because the two mutations are on opposite sides of the binding cleft.

Cysteine mutations were prepared in plasmid PSN5182 using the Quikchange site-directed mutagenesis kit (Stratagene), and then amplified by polymerase chain reaction (PCR). PCR products were transformed into the *E. coli* strain DH5α (library efficiency, Invitrogen). The plasmid was purified using Qiaprep kit (Qiagen) and analyzed by 1%-agarose gel electrophoresis. The sequences of plasmid DNA containing the desired changes were confirmed by DNA sequencing (MWG-Biotech). The DNA was transformed into *E. coli* strain ANCC75 for protein expression.

The genes were expressed in *E. coli* and proteins were purified essentially as described in references 25 & 31. In some cases 1 mM dithiothreitol was added to all buffers from the time of the osmotic shock through to the stock storage buffer. The protein was stored at −80° C. in aliquots at ~1 mM concentration.

Labelling Mutant PBPs.

The exact time and conditions for labelling of cysteine mutants depended both on the reactivity of the label and how exposed was the thiol. Conditions given below are for labelling of the A17C-A197C mutant. Prior to labelling, fresh dithiothreitol (to 10 mM) was added to the protein (at ~1 mM) which was then desalted by gel filtration on a PD10 column (Amersham) in degassed 10 mM Tris.HCl pH 7.6, 1 mM $MgCl_2$.

The protein was labelled on a scale of 20 mg. The following solution was incubated for 15 minutes at 20° C. under nitrogen in 50 mM Tris.HCl pH 8.1 to remove Pi: 100 μM mutant PBP, 200 μM 7-methylguanosine, 0.2 unit $mL^{-1}$ PNPase. The protein was then labelled by adding 800 μM 6-IATR [32] (from a stock solution of ~20 mM in dimethylformamide). The solution was mixed end-over-end with protection from light at 22° C. for 2 h. The solution was made 1.6 mM in sodium 2-mercaptoethanesulfonate and incubated for 20 minutes. It was then filtered through a 0.2 μm polysulfone membrane. Rhodamine that was not bound to the protein was removed by gel filtration on a 100 mL P4 column (Bio-Rad), equilibrated in 10 mM Tris-HCl pH 8.0 at room temperature. The labelled protein was then purified by ion exchange chromatography at 4° C. on a 20 mL column of Q Sepharose FF, equilibrated in 10 mM Tris.HCl pH 8.0 at 4° C., using a 400 mL gradient from 0 to 200 mM NaCl in 10 mM Tris.HCl pH 8.0.

After concentration by ultrafiltration through a YM10 membrane (Amicon), the labelled protein was purified further at room temperature on a MonoQ HR 10/10 column (Amersham), equilibrated in 10 mM Tris.HCl pH 8.5, 15 mM KCl. Protein was eluted at 2.5 mL $min^{-1}$ with a 150 mL gradient in 10 mM Tris.HCl pH 8.5 from 15 mM NaCl to 30 mM NaCl. The peak corresponding to doubly labelled protein was concentrated as above, diluted with several volumes of 10 mM Tris.HCl pH 8.0, reconcentrated, and then stored at −80° C. in aliquots at ~1 mM.

It became apparent that the published extinction coefficient for a small molecule thiol adduct of 6-IATR (52000 $M^{-1}$ $cm^{-1}$ at its isosbestic point of 528 nm) [32] is not applicable to Rhodamine-PBP for two reasons. Firstly, when this extinction coefficient was used to calculate protein concentration, the apparent binding capacity from Pi titrations (see below) was greater than 100%. Secondly, the isosbestic point in the absorbance spectrum of Rhodamine-PBP was determined using different concentrations of Pi and is 526 nm. Thus an extinction coefficient of 108 $mM^{-1}$ $cm^{-1}$ at 526 nm was calculated for the doubly labeled protein, assuming 100% binding capacity for Pi in such titrations. The value is based on an average of 6 titrations. The concentrations of other Rhodamine-PBP samples were then calculated from this extinction coefficient.

The molecular mass of unlabeled and labeled protein was determined by electrospray mass spectrometry as described previously [25]. The reactivity of thiols of unlabeled protein was determined by reaction with DTNB as described previously [10].

Three thiol-selective rhodamines were used in labeling tests: two iodoacetamides, 6-IATR and 5-IATR, and one maleimide, Rhodamine Red™ C2 ('RRC2M, from Invitrogen). It became apparent that the signal response depends not only the position of the rhodamines, but also on the degree of purity of the final, doubly labeled product. The latter is dependent on the ease of labeling, as singly or triply labeled protein has an unpaired rhodamine and so high fluorescence (see below), and also on the resolution obtained during the purification.

All five double mutation PBPs were tested with 6-IATR. The two best mutants were the K229C-E302C (8.5-fold fluorescence increase with Pi) and A17C-A197C (18-fold increase) and these were chosen for further study. Two other fluorophores were tested with the best mutant, A17C-A197C. The RRC2M did not label well and gave a product with little fluorescence change. 5-IATR labeled the two cysteines of this mutant, but the product gave ~2.5-fold increase.

Mass spectrometry data suggested that it is possible to label an amine with 6-IATR, albeit slowly, in addition to labelling thiols. Incomplete labelling is also possible. Either of these unwanted labelling patterns may give rise to protein-attached rhodamine that is unlikely to have a second rhodamine to pair with, and which will therefore have high fluorescence regardless of Pi-binding. Such labels would contribute significant background fluorescence intensity. Chromatography revealed the presence of single-, double- and triple-labelled species and so, to avoid these problems, the doubly-labelled molecule was prepared in pure form by (a) optimizing the labelling conditions to avoid single- and triple-labelled forms, and (b) using ion exchange chromatography to remove any unwanted species. Electrospray mass spectrometry showed that these methods gave a pure 6-IATR-labelled 17/197 mutant.

Absorbance and Fluorescence Measurements

Absorbance spectra were obtained using a Beckman DU640 spectrophotometer. Fluorescence measurements were obtained on a Perkin Elmer LS50B or Cary Eclipse fluorimeter with xenon lamp. Stopped flow experiments were carried out on a HiTech SF61MX apparatus, with a mercury-xenon lamp and HiTech IS-2 software, a monochromator and 4 mm slits on the excitation light (550 nm for rhodamine) and a 570 nm cut-off filter on the emission. The stated concentrations are those in the mixing chamber, unless stated otherwise.

Absorbance spectra were obtained in 10 mM PIPES pH 7.0 buffer with 3.8 μM protein and either 125 μM Pi (+Pi) or a phosphate mop (2.5 unit/ml PNPase, 200 μM MEG) (−Pi). These spectra allowed the concentration of the protein to be calculated based on an extinction coefficient for the double labeled protein of 108 $mM^{-1}$ $cm^{-1}$ at 526 nm (isosbestic point)—see above.

Fluorescence spectra were obtained under the same conditions. Excitation was at 555 nm. The fluorescence signals were normalised to 100%, representing the maximum intensity in the presence of Pi.

Figure 2:
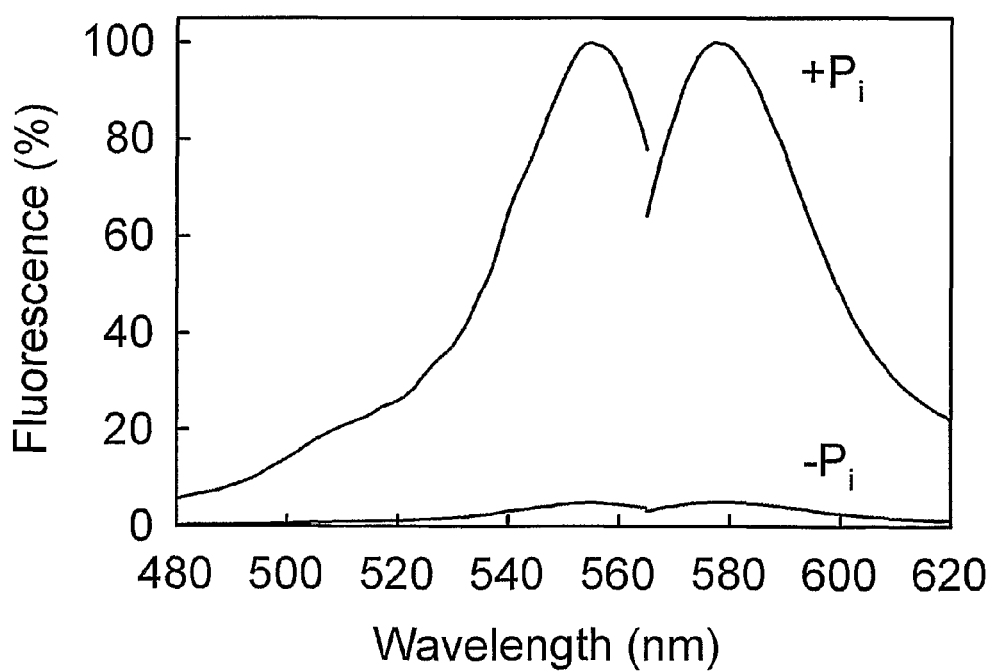
FIG. 2 shows its fluorescence spectrum.

In terms of detectable changes between Pi-free and Pi-bound forms, the best results were obtained with the 17/197 mutant. With this mutant, RRC2M showed little fluorescence change. 5-IATR gave a change seven-fold less than with 6-IATR, even though the two mutants were labelled to the same extent. The absorbance and emission spectra for the 6-IATR-labeled 17/197 mutant are shown in FIGS. 1 and 2. The better results with the iodo-linked labels may be explained by the extra bulk of the maleimide over the iodoacetamide and possibly by the presence of diasteroisomers from maleimide labeling.

The 17/197 mutant labelled with 6-IATR was studied in further detail, and is referred to below simply as 'rhodamine-PBP'. The fluorescence of this Rhodamine-PBP is much lower than that expected for two independent monomers, presumably because the two rhodamines can interact via stacking. As shown in FIG. 1, the absorbance spectrum of this purified Rhodamine-PBP shows a change on Pi-binding, with the peak at $\lambda_{max}$ 554 nm increasing ~2.5-fold on saturation with Pi. There is a concomitant decrease in the peak at 515 nm. The fluorescence spectrum also shows a large change on Pi-binding (FIG. 2), with emission at 578 nm ($\lambda_{max}$) increasing up to ~30-fold. The amplitude of the increase depends on the resolution of different labeled species by the final ion exchange column and is typically ~18-fold. The fluorescence changes at pH 6.5 and 8.0 are similar to that at pH 7.0. The excitation spectrum has a maximum that coincides with the absorbance peak at 554 nm. There is much less fluorescence excitation at the position of the second absorbance peak at 515 nm. The absorbance spectra suggest that there is almost complete rhodamine dimer formation in the absence of Pi, which ensures that the fluorescence is very low. In the presence of Pi, the conformation change translates into a change in rhodamine stacking, with concomitant increase in fluorescence.

Figure 3:
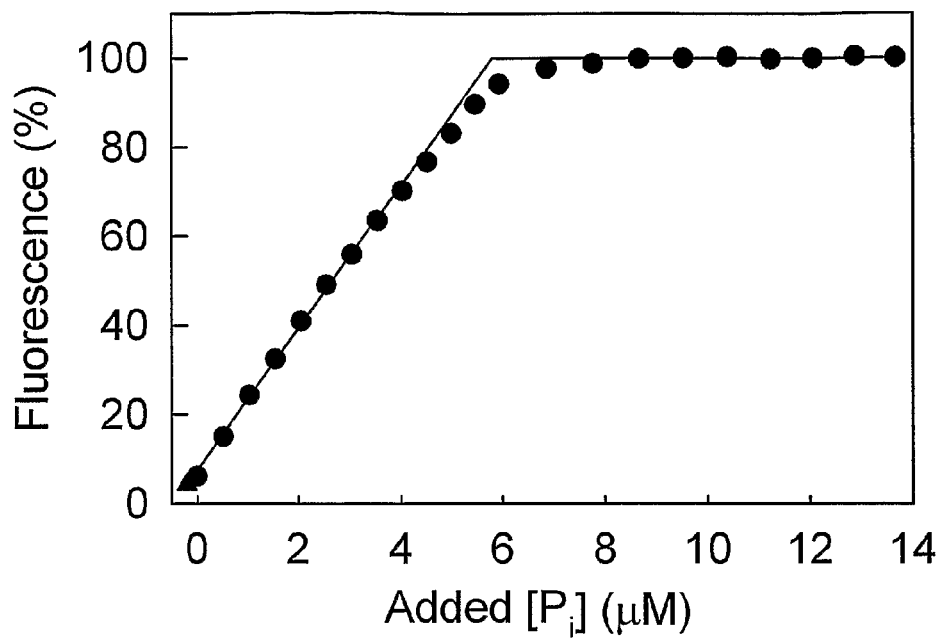
FIG. 3 shows the titration of Pi with the same preferred protein.
Figure 5:
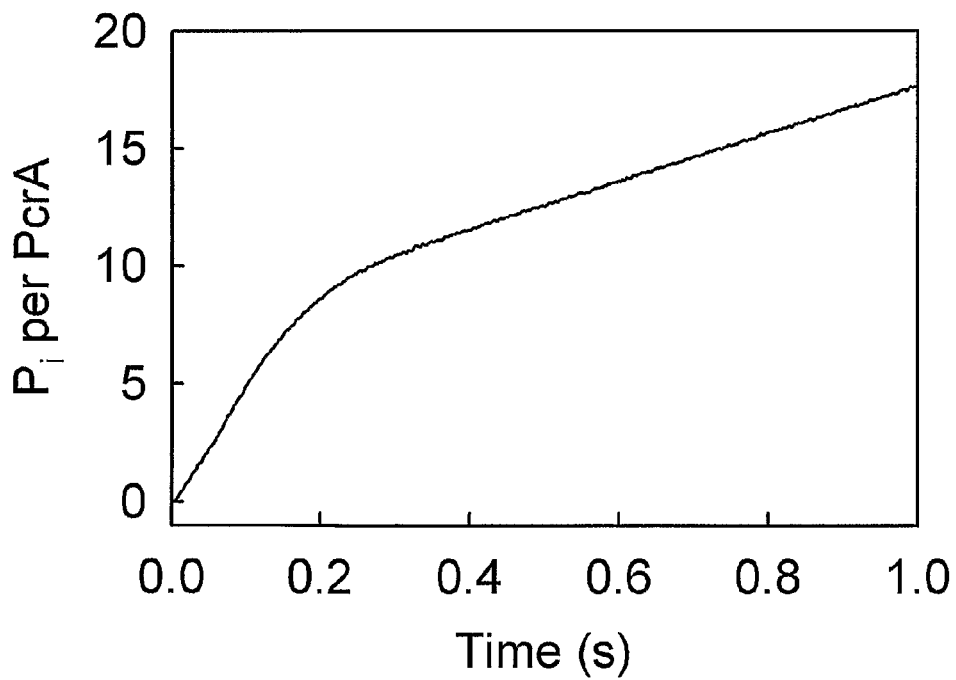
FIG. 5 shows that Rhodamine-PBP can successfully monitor Pi in real time.

The purified protein was titrated with Pi at 20° C., as shown in FIG. 3. Aliquots of Pi were added to 6 μM rhodamine-PBP and the fluorescence was measured at 575 nm, with excitation at 555 nm (circles). The data are normalized to 100% for the fluorescence at high [Pi]. The triangle represents the fluorescence after a rhodamine-PBP solution was treated with a phosphate mop (2.5 unit ml$^{-1}$ PNPase, 200 μM MEG) for 15 minutes. This fluorescence represents the value when approximately Pi-free. The lines shown in FIG. 3 are a best fit to data from 0 to 4 μM added Pi, and a horizontal line. The intercept of these two lines is a measure of the capacity of the rhodamine-PBP for Pi [31].

FIG. 3 shows that fluorescence increases linearly with Pi over most of its range, and essentially all the sites in rhodamine-PBP can be bound similarly with Pi. The binding capacity is ~100%, after taking into account the small amount of Pi present through contamination. This stoichiometry is higher than seen with MDCC-PBP [25], where a similar titration typically shows 75% capacity. The likely explanation for this difference is the presence of diastereoisomers of MDCC-PBP, as the linkage is via a chiral centre on a succinimide [29]. The diastereoisomers have different responses to Pi binding [25], giving rise to an apparently reduced activity. Using an iodoacetamide linker does not give a chiral centre, thereby avoiding this issue.

The doubly labeled K229C-E302C protein shows a similar set of absorbance and fluorescence results albeit with a lower fluorescence enhancement. The fluorescence titration with Pi shows the protein is ~100% active. These distinct changes in the absorbance spectrum suggest the basis of the main fluorescence change for this mutant is also the change in rhodamine stacking.

Figure 4:
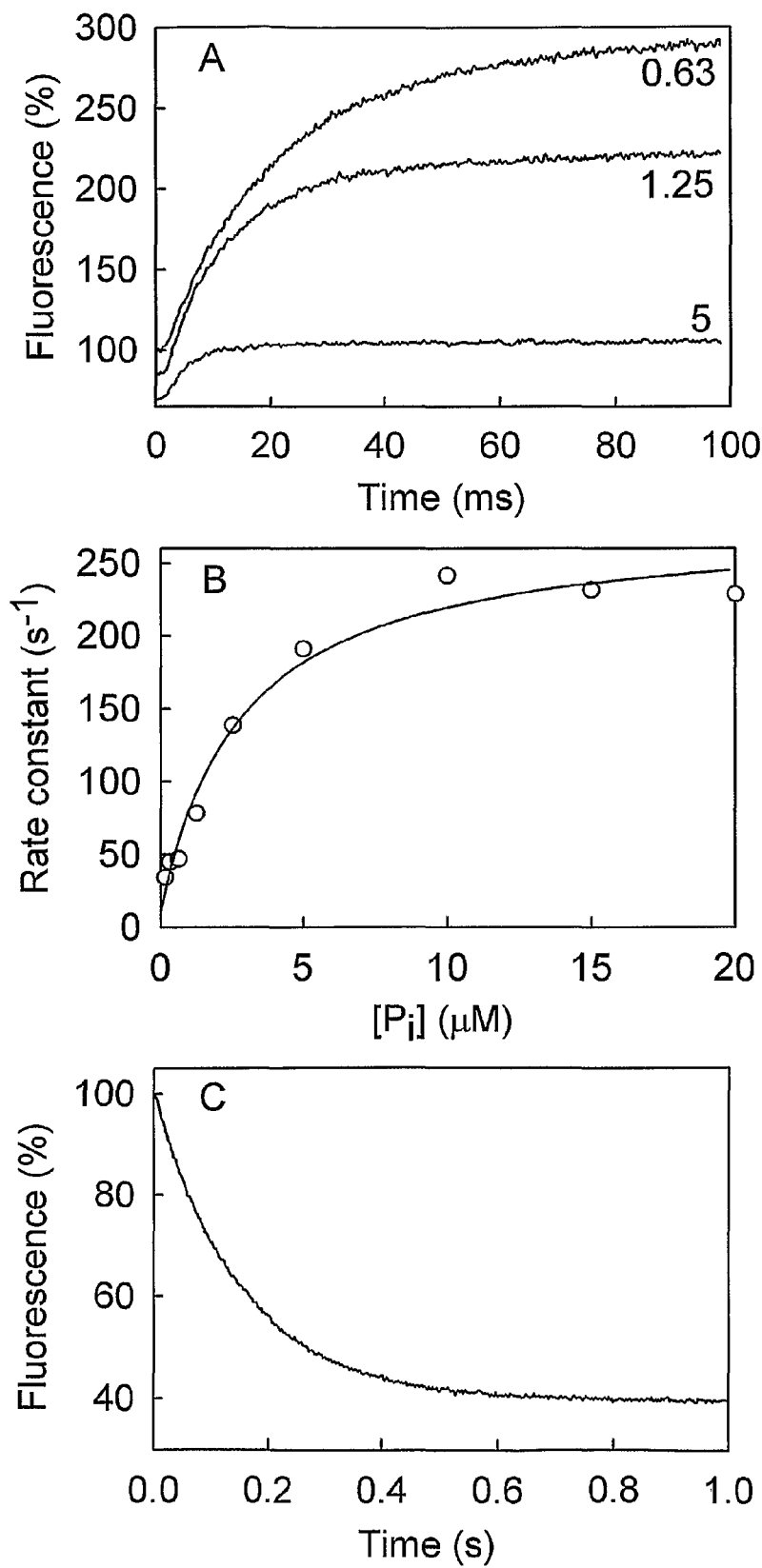
FIG. 4 shows the kinetics of Pi association with and dissociation from the same preferred protein.
Figure 6:
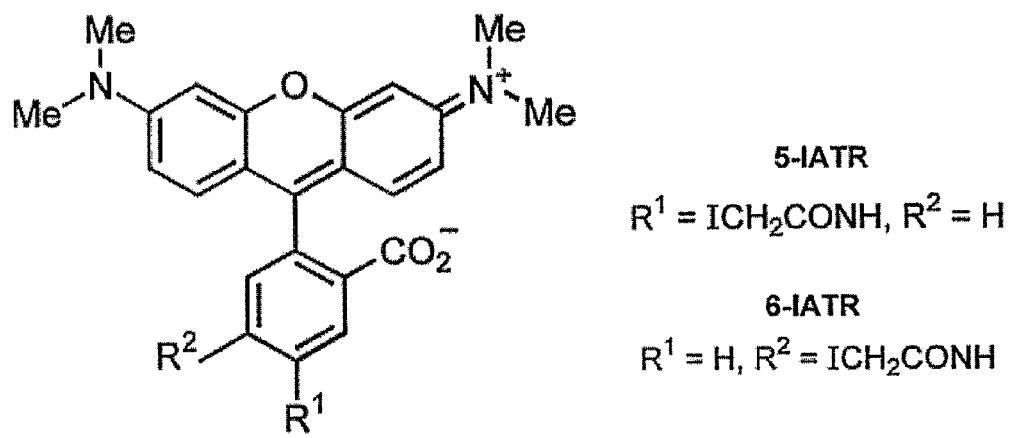
FIG. 6 shows the structures of various rhodamines including 5-IATR and 6-IATR that are suitable for use with the invention.
Figure 6:
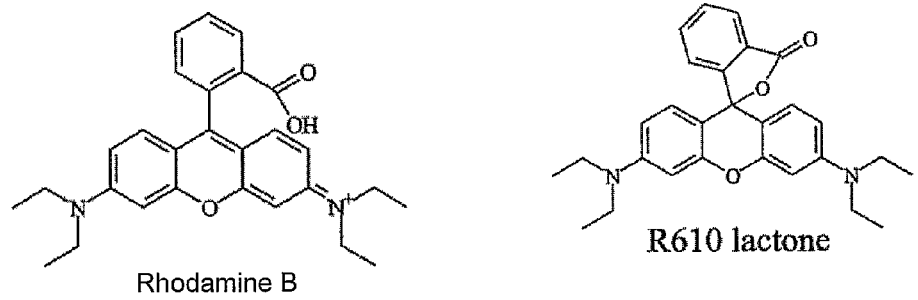
Figure 6:
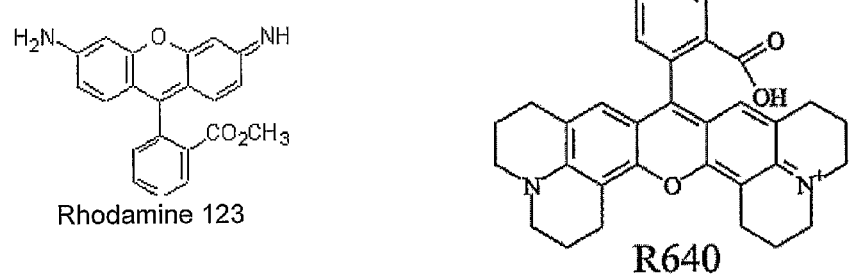

A stopped-flow apparatus was used to determine association and dissociation kinetics of Pi from rhodamine-PBP. Results are shown in FIG. 4.

For a measurement of association kinetics, 0.1 μM rhodamine-PBP was rapidly mixed with various concentrations of Pi at 10° C. in 10 mM PIPES, pH 7.0. A representative set of fluorescence traces is shown in FIG. 4A, all normalized to 100% for the initial intensity, but offset by 15% from each other. The micromolar concentrations of Pi are shown in FIG. 4A for each trace. As the concentration of Pi and the rate increase, a significant proportion of the fluorescence trace is lost in the dead time of the stopped-flow instrument, causing an apparent decrease in intensity. The data could be fitted to a hyperbola, as shown in FIG. 4B.

It is apparent that the rate reaches a limiting high value. This can be interpreted in terms of a two-step mechanism, binding itself (step 1), then a conformation change (step 2):

The fluorescence change occurs in step 2 and is likely to be concomitant with the closure of the binding cleft. It is this process that limits the overall rate at high Pi concentration. The data in FIG. 4B fitted to a hyperbola give $1/K_1=2.2$ μM and $k_{+2}+k_{-2}=267$ s$^{-1}$ (at 10° C.).

Dissociation kinetics were measured similarly, by mixing a pre-formed complex of Pi with the rhodamine-PBP (0.25 μM rhodamine-PBP containing 0.06 μM bound-Pi) with a large excess (10 μM) wild-type PBP, using the same conditions as above. 2.5 μM BSA was present with the Rhodamine-PBP to minimize any adsorption to surfaces. 0.25 unit mL$^{-1}$ PNPase and 100 μM 7-methylguanosine were present with the wild-type PBP to ensure that it was free of Pi prior to mixing. The results are shown in FIG. 4C. The kinetics of the fluorescence change are limited by the Pi dissociation rate, as shown by varying the concentration of wild-type PBP. A best fit exponential gave a rate of 6.6 s$^{-1}$, as binding to wild-type PBP is fast.

The kinetic data show that the association kinetics of rhodamine-PBP (at 10° C.) are slower than that found with MDCC-PBP at 5° C. This may be because the rhodamine dimer must be disrupted, providing a small additional barrier for cleft closure to occur. The overall dissociation constant is given by $k_{-2}/k_{+2}K_1$, which is 0.06 μM. The tightness of binding is similar to that of MDCC-PBP.

Comparison with Commercially Available Phosphate Assay Kits

A comparison of the rhodamine-PBP assay with existing phosphate assay kits is shown below.

| Assay | Phosphate detection concentration | Kinetics | Absorbance |
|---|---|---|---|
| Quantichrom (Chemical) | 0.3 mM-50 mM | slow | 620 nm |
| Enzchek (Enzymatic) | 2 μM-150 μM | medium | 360 nm |
| rhodamine-PBP | 10 nM-1 mM | very fast | 575 nm |
| MDCC-PBP | 10 nM-1 mM | very fast | 465 nm |

Discussion

Thus the specific labeling of a double cysteine mutant PBP by a rhodamine can produce a species whose fluorescence responds to binding Pi. The size of the fluorescence change in response to Pi binding depends on several factors. The first is the distance and accessibility between thiol-attached rhodamines and the movement during the Pi-associated conformation change. Examination of the crystal structures provided an initial assessment of this, taking into account the covalent structure of the labels to determine suitable distances that might allow rhodamine-rhodamine interaction. Secondary effects, such as possible flexibility on the protein or interaction with amino acid side chains, may also be important.

Factors such as good labeling conditions and the ability to separate out other labeled species that are likely to have high fluorescence are important. The protocol described typically gives a product with ~18-fold fluorescence change. The best batch of product gave 30-fold, presumably due to the almost complete elimination of high fluorescence impurities.

When the labeling sites are on the side of the molecule opposite from the binding cleft, the Pi site is unmodified. As described above, these rear faces of the two domains move apart when Pi binds to its site, so the α-carbons of the two labeled cysteines get separated further. This side of the protein is relatively open, so that this distance change might be expected to be the main factor in determining a change in rhodamine stacking. With one such labeled mutant (K229C-E302C), an 8.5-fold increase in rhodamine fluorescence occurs on Pi binding, when the α-carbons move from 1.2 to 1.7 nm apart. In this case both labeling sites are well away from the binding site and so may be neither affected by, or affect the binding of Pi.

The A17C-A197C mutant protein labeled with 6-IATR, gave up to 30-fold increase in fluorescence. The α-carbons of these two amino acids are 1.6 and 1.3 nm apart in Pi-free and Pi-bound conformations of PBP respectively. This is due to the binding cleft closure with each mutation being on opposite sides of the cleft. The absorbance spectra of the purified product, Rhodamine-PBP (FIG. 1) suggest that there is almost complete dimer formation in the absence of Pi and this ensures that the fluorescence is very low. The large increase in fluorescence suggests that there is a significant change in rhodamine-rhodamine interaction on Pi binding. Although the α-carbons get closer on Pi binding, the 197 position becomes partly buried, presumably constraining its attached rhodamine so that it can no longer interact well with the A17C rhodamine.

It will be understood that the invention has been described by way of example only and modifications may be made whilst remaining within the scope and spirit of the invention.

REFERENCES

The Contents of which are hereby Incorporated by Reference

[1] EP-A-0159513.
[2] Webb et al. (1992) *PNAS* 89:4884-7.
[3] Magota et al. (1984) *J. Bacteriol.* 157:909-17.
[4] Surin et al. (1984) *J. Bacteriol.* 157:772-8.
[5] Luecke & Quiocho (1990) *Nature* 347, 402-406
[6] Ledvina et al. (1996) *PNAS* 93:6786-91.
[7] EP-A-0715721.
[8] Morales et. al. (2006) *Structure* 14:601-609
[9] Tam & Saier (1993) *Microbiol. Rev.* 57:320-46.
[10] Quiocho & Ledvina (1996) *Mol. Microbiol.* 20:17-25
[11] Vyas et. al. (2003) *Structure* 11, 765-774
[12] Fukami-Kobayashi et al (1999) *J. Mol. Biol.*, 286, 279-290
[13] Yao et al. (1996) *Biochemistry* 35:2079-85.
[14] Wang et al. (1997) *Nat Struct Biol* 4:519.
[15] Wang et al. (1994) *J Biol Chem* 269:25091-4.
[16] Ledvina et al. (1998) *Protein Sci* 7:2550-9.
[17] Rohatgi & Singhal (1966) *J. Phys. Chem.* 70:1695-701.
[18] Förster & König (1957) *Z. Elektrochem.* 61:344-8.
[19] Selwyn & Steinfeld (1972) *J. Phys. Chem.* 76:762-74.
[20] Chambers et al. (1974) *J. Phys. Chem.* 78:380-387.
[21] Blackman et al. (2002) *Biochemistry* 41:12244-52
[22] Dietrich et al. (2002) *Rev. Mol. Biotechnol.* 82:211-31
[23] Hamman et al. (1996) *J. Biol. Chem.* 271:7568-73
[24] Kasha (1963) *Radiat. Res*, 20, 55-71
[25] Brune et al. (1998) *Biochemistry* 37:10370-80.
[26] *Bioconjugate Techniques*. Hermanson (1996). ISBN 0-12-342336-8.
[27] Brune et al. (1994) *Biochemistry* 33:8262-71.
[28] Salins et al. (2004) *Sensors and Actuators B* 97:81-9.
[29] Hirshberg et al. (1998) *Biochemistry* 37:10381-5
[30] Nixon et al. (1995) *Biochemistry* 34:15592-8.
[31] Webb (2003) *A fluorescent sensor to assay inorganic phosphate in Kinetic analysis: a practical approach* (ed. Johnson) pp 131-152, Oxford University Press, Oxford, UK.
[32] Corrie & Craik (1994) *J. Chem. Soc., Perkin Trans. I:* 2967-74.

---

The invention claimed is:

1. A labeled phosphate-binding protein (PBP) that undergoes a conformational change from an initial conformation to a final conformation upon binding of phosphate, wherein the phosphate-binding protein is selected from the group consisting of SEQ ID NO: 1, 2, 3, 4 and 15, and wherein the phosphate-binding protein is derivatized with a first label and a second label which can exhibit molecular stacking, wherein the molecular stacking is altered on changing from one conformation to the other and wherein the first label and second label each comprise fluorophores.

2. The labeled protein of claim 1, wherein the first and second labels can exhibit molecular stacking either (a) in the initial conformation but not in the final conformation, or (b) in the final conformation but not in the initial conformation.

3. The labeled protein of claim 1, wherein the phosphate binding protein includes two cysteine substitutions, for attachment of the first and second labels.

4. The labeled protein of claim 3 having an amino acid sequence selected from the group consisting of:
SEQ ID NO: 2, SEQ ID NO 3 and SEQ ID NO 4.

5. The labeled protein of claim 1, wherein the first and second labels include a xanthene group.

6. The labeled protein of claim 5, wherein the first and second labels include a rhodamine.

7. The labeled protein of claim 6, wherein the rhodamine is 6-IATR.

8. The labeled protein of claim 1, wherein the first and second labels include fluorophores attached to the protein via haloacetamide linkers.

9. The labeled protein of claim 1, wherein the first and second labels can stack in the initial conformation.

10. The labeled protein of claim 1, wherein the first and second labels can stack in the final conformation.

11. A method for detecting inorganic phosphate in a sample, comprising the steps of: (i) mixing the sample with the protein of claim 1, and (ii) detecting a change in the mixture arising from interaction between the inorganic phosphate and the PBP, wherein the change detected in step (ii) correlates with the concentration of inorganic phosphate in the sample.

12. A kit comprising the labeled protein of claim 1, and a phosphate mop.

* * * * *

SEQUENCE LISTING

```
<160> NUMBER OF SEQ ID NOS: 23

<210> SEQ ID NO 1
<211> LENGTH: 346
<212> TYPE: PRT
<213> ORGANISM: E. Coli

<400> SEQUENCE: 1

Met Lys Val Met Arg Thr Thr Val Ala Thr Val Val Ala Ala Thr Leu
1               5                   10                  15

Ser Met Ser Ala Phe Ser Val Phe Ala Glu Ala Ser Leu Thr Gly Ala
                20                  25                  30

Gly Ala Thr Phe Pro Ala Pro Val Tyr Ala Lys Trp Ala Asp Thr Tyr
            35                  40                  45

Gln Lys Glu Thr Gly Asn Lys Val Asn Tyr Gln Gly Ile Gly Ser Ser
        50                  55                  60

Gly Gly Val Lys Gln Ile Ile Ala Asn Thr Val Asp Phe Gly Ala Ser
65                  70                  75                  80

Asp Ala Pro Leu Ser Asp Glu Lys Leu Ala Gln Glu Gly Leu Phe Gln
                85                  90                  95

Phe Pro Thr Val Ile Gly Gly Val Val Leu Ala Val Asn Ile Pro Gly
                100                 105                 110

Leu Lys Ser Gly Glu Leu Val Leu Asp Gly Lys Thr Leu Gly Asp Ile
```

```
            115                 120                 125
Tyr Leu Gly Lys Ile Lys Lys Trp Asp Asp Glu Ala Ile Ala Lys Leu
130                 135                 140

Asn Pro Gly Leu Lys Leu Pro Ser Gln Asn Ile Ala Val Val Arg Arg
145                 150                 155                 160

Ala Asp Gly Ser Gly Thr Ser Phe Val Phe Thr Ser Tyr Leu Ala Lys
                165                 170                 175

Val Asn Glu Glu Trp Lys Asn Asn Val Gly Thr Gly Ser Thr Val Lys
                180                 185                 190

Trp Pro Ile Gly Leu Gly Gly Lys Gly Asn Asp Gly Ile Ala Ala Phe
            195                 200                 205

Val Gln Arg Leu Pro Gly Ala Ile Gly Tyr Val Glu Tyr Ala Tyr Ala
210                 215                 220

Lys Gln Asn Asn Leu Ala Tyr Thr Lys Leu Ile Ser Ala Asp Gly Lys
225                 230                 235                 240

Pro Val Ser Pro Thr Glu Glu Asn Phe Ala Asn Ala Ala Lys Gly Ala
                245                 250                 255

Asp Trp Ser Lys Thr Phe Ala Gln Asp Leu Thr Asn Gln Lys Gly Glu
                260                 265                 270

Asp Ala Trp Pro Ile Thr Ser Thr Phe Ile Leu Ile His Lys Asp
            275                 280                 285

Gln Lys Lys Pro Glu Gln Gly Thr Glu Val Leu Lys Phe Phe Asp Trp
            290                 295                 300

Ala Tyr Lys Thr Gly Ala Lys Gln Ala Asn Asp Leu Asp Tyr Ala Ser
305                 310                 315                 320

Leu Pro Asp Ser Val Val Glu Gln Val Arg Ala Ala Trp Lys Thr Asn
                325                 330                 335

Ile Lys Asp Ser Ser Gly Lys Pro Leu Tyr
                340                 345

<210> SEQ ID NO 2
<211> LENGTH: 321
<212> TYPE: PRT
<213> ORGANISM: Artificial Sequence
<220> FEATURE:
<223> OTHER INFORMATION: Synthetic Construct

<400> SEQUENCE: 2

Glu Ala Ser Leu Thr Gly Ala Gly Ala Thr Phe Pro Ala Pro Val Tyr
1               5                   10                  15

Ala Lys Trp Ala Asp Thr Tyr Gln Lys Glu Thr Gly Asn Lys Val Asn
                20                  25                  30

Tyr Gln Gly Ile Gly Ser Ser Gly Gly Val Lys Gln Ile Ile Ala Asn
            35                  40                  45

Thr Val Asp Phe Gly Ala Ser Asp Ala Pro Leu Ser Asp Glu Lys Leu
50                  55                  60

Ala Gln Glu Gly Leu Phe Gln Phe Pro Thr Val Ile Gly Gly Val Val
65                  70                  75                  80

Leu Ala Val Asn Ile Pro Gly Leu Lys Ser Gly Glu Leu Val Leu Asp
                85                  90                  95

Gly Lys Thr Leu Gly Asp Ile Tyr Leu Gly Lys Ile Lys Lys Trp Asp
            100                 105                 110

Asp Glu Ala Ile Ala Lys Leu Asn Pro Gly Leu Lys Leu Pro Ser Gln
            115                 120                 125

Asn Ile Ala Val Val Arg Arg Ala Asp Gly Ser Gly Thr Ser Phe Val
130                 135                 140
```

Phe Thr Ser Tyr Leu Ala Lys Val Asn Glu Trp Lys Asn Asn Val
145                 150                 155                 160

Gly Thr Gly Ser Thr Val Lys Trp Pro Ile Gly Leu Gly Lys Gly
                165                 170                 175

Asn Asp Gly Ile Ala Ala Phe Val Gln Arg Leu Pro Gly Ala Ile Gly
            180                 185                 190

Tyr Val Glu Tyr Ala Tyr Ala Lys Gln Asn Asn Leu Ala Tyr Thr Lys
        195                 200                 205

Leu Ile Ser Ala Asp Gly Lys Pro Val Ser Pro Thr Glu Glu Asn Phe
    210                 215                 220

Ala Cys Ala Ala Lys Gly Ala Asp Trp Ser Lys Thr Phe Ala Gln Asp
225                 230                 235                 240

Leu Thr Asn Gln Lys Gly Glu Asp Ala Trp Pro Ile Thr Ser Thr Thr
                245                 250                 255

Phe Ile Leu Ile His Lys Asp Gln Lys Lys Pro Glu Gln Gly Thr Glu
            260                 265                 270

Val Leu Lys Phe Phe Asp Trp Ala Tyr Lys Thr Gly Ala Lys Gln Ala
        275                 280                 285

Asn Asp Leu Asp Tyr Ala Ser Leu Pro Asp Cys Val Val Glu Gln Val
    290                 295                 300

Arg Ala Ala Trp Lys Thr Asn Ile Lys Asp Ser Ser Gly Lys Pro Leu
305                 310                 315                 320

Tyr

<210> SEQ ID NO 3
<211> LENGTH: 321
<212> TYPE: PRT
<213> ORGANISM: Artificial Sequence
<220> FEATURE:
<223> OTHER INFORMATION: Synthetic Construct

<400> SEQUENCE: 3

Glu Ala Ser Leu Thr Gly Ala Gly Ala Thr Phe Pro Ala Pro Val Tyr
1               5                   10                  15

Cys Lys Trp Ala Asp Thr Tyr Gln Lys Glu Thr Gly Asn Lys Val Asn
                20                  25                  30

Tyr Gln Gly Ile Gly Ser Ser Gly Gly Val Lys Gln Ile Ile Ala Asn
            35                  40                  45

Thr Val Asp Phe Gly Ala Ser Asp Ala Pro Leu Ser Asp Glu Lys Leu
        50                  55                  60

Ala Gln Glu Gly Leu Phe Gln Phe Pro Thr Val Ile Gly Gly Val Val
65                  70                  75                  80

Leu Ala Val Asn Ile Pro Gly Leu Lys Ser Gly Glu Leu Val Leu Asp
                85                  90                  95

Gly Lys Thr Leu Gly Asp Ile Tyr Leu Gly Lys Ile Lys Lys Trp Asp
            100                 105                 110

Asp Glu Ala Ile Ala Lys Leu Asn Pro Gly Leu Lys Leu Pro Ser Gln
        115                 120                 125

Asn Ile Ala Val Val Arg Arg Ala Asp Gly Ser Gly Thr Ser Phe Val
    130                 135                 140

Phe Thr Ser Tyr Leu Ala Lys Val Asn Glu Glu Trp Lys Asn Asn Val
145                 150                 155                 160

Gly Thr Gly Ser Thr Val Lys Trp Pro Ile Gly Leu Gly Gly Lys Gly
                165                 170                 175

Asn Asp Gly Ile Ala Ala Phe Val Gln Arg Leu Pro Gly Ala Ile Gly

```
            180                 185                 190
Tyr Val Glu Tyr Cys Tyr Ala Lys Gln Asn Asn Leu Ala Tyr Thr Lys
            195                 200                 205

Leu Ile Ser Ala Asp Gly Lys Pro Val Ser Pro Thr Glu Glu Asn Phe
        210                 215                 220

Ala Asn Ala Ala Lys Gly Ala Asp Trp Ser Lys Thr Phe Ala Gln Asp
225                 230                 235                 240

Leu Thr Asn Gln Lys Gly Glu Asp Ala Trp Pro Ile Thr Ser Thr Thr
                245                 250                 255

Phe Ile Leu Ile His Lys Asp Gln Lys Lys Pro Glu Gln Gly Thr Glu
                260                 265                 270

Val Leu Lys Phe Phe Asp Trp Ala Tyr Lys Thr Gly Ala Lys Gln Ala
            275                 280                 285

Asn Asp Leu Asp Tyr Ala Ser Leu Pro Asp Ser Val Val Glu Gln Val
            290                 295                 300

Arg Ala Ala Trp Lys Thr Asn Ile Lys Asp Ser Ser Gly Lys Pro Leu
305                 310                 315                 320

Tyr

<210> SEQ ID NO 4
<211> LENGTH: 321
<212> TYPE: PRT
<213> ORGANISM: Artificial Sequence
<220> FEATURE:
<223> OTHER INFORMATION: Synthetic Construct

<400> SEQUENCE: 4

Glu Ala Ser Leu Thr Gly Ala Gly Ala Thr Phe Pro Ala Pro Val Tyr
1               5                   10                  15

Ala Lys Trp Ala Asp Thr Tyr Gln Lys Glu Thr Gly Asn Lys Val Asn
            20                  25                  30

Tyr Gln Gly Ile Gly Ser Ser Gly Gly Val Lys Gln Ile Ile Ala Asn
        35                  40                  45

Thr Val Asp Phe Gly Ala Ser Asp Ala Pro Leu Ser Asp Glu Lys Leu
    50                  55                  60

Ala Gln Glu Gly Leu Phe Gln Phe Pro Thr Val Ile Gly Gly Val Val
65                  70                  75                  80

Leu Ala Val Asn Ile Pro Gly Leu Lys Ser Gly Glu Leu Val Leu Asp
                85                  90                  95

Gly Lys Thr Leu Gly Asp Ile Tyr Leu Gly Lys Ile Lys Lys Trp Asp
            100                 105                 110

Asp Glu Ala Ile Ala Lys Leu Asn Pro Gly Leu Lys Leu Pro Ser Gln
        115                 120                 125

Asn Ile Ala Val Val Arg Arg Ala Asp Gly Ser Gly Thr Ser Phe Val
    130                 135                 140

Phe Thr Ser Tyr Leu Ala Lys Val Asn Glu Glu Trp Lys Asn Asn Val
145                 150                 155                 160

Gly Thr Gly Ser Thr Val Lys Trp Pro Ile Gly Leu Gly Gly Lys Gly
                165                 170                 175

Asn Asp Gly Ile Ala Ala Phe Val Gln Arg Leu Pro Gly Ala Ile Gly
            180                 185                 190

Tyr Val Glu Tyr Ala Tyr Ala Lys Gln Asn Asn Leu Ala Tyr Thr Lys
        195                 200                 205

Leu Ile Ser Ala Asp Gly Lys Pro Val Ser Pro Thr Glu Glu Asn Phe
    210                 215                 220
```

-continued

Ala Asn Ala Ala Cys Gly Ala Asp Trp Ser Lys Thr Phe Ala Gln Asp
225 230 235 240

Leu Thr Asn Gln Lys Gly Glu Asp Ala Trp Pro Ile Thr Ser Thr Thr
245 250 255

Phe Ile Leu Ile His Lys Asp Gln Lys Lys Pro Glu Gln Gly Thr Glu
260 265 270

Val Leu Lys Phe Phe Asp Trp Ala Tyr Lys Thr Gly Ala Lys Gln Ala
275 280 285

Asn Asp Leu Asp Tyr Ala Ser Leu Pro Asp Ser Val Val Cys Gln Val
290 295 300

Arg Ala Ala Trp Lys Thr Asn Ile Lys Asp Ser Ser Gly Lys Pro Leu
305 310 315 320

Tyr

<210> SEQ ID NO 5
<211> LENGTH: 297
<212> TYPE: PRT
<213> ORGANISM: Burkholderia

<400> SEQUENCE: 5

Met Ser Glu Pro Ile Met Asn Phe Pro Gly Pro Asp Gly Ala Ala Leu
1 5 10 15

Asp Ala Met Arg Asn Arg Leu Gln Arg Lys Arg Lys Ala Val Asn Ala
20 25 30

Ile Ala Leu Thr Ala Ser Leu Gly Ala Met Ala Phe Gly Leu Leu Trp
35 40 45

Leu Val Trp Ile Leu Tyr Thr Thr Val His Leu Gly Val Gly Gly Leu
50 55 60

Ser Leu Gln Leu Phe Thr Glu Ser Thr Pro Ala Pro Asn Thr Glu Gly
65 70 75 80

Gly Gly Leu Ala Asn Ala Ile Val Gly Ser Leu Leu Leu Cys Gly Phe
85 90 95

Gly Thr Leu Val Gly Thr Pro Ile Gly Ile Leu Ala Gly Val Tyr Leu
100 105 110

Ala Glu Tyr Gly Gln Lys Asn Leu Leu Ala Ser Thr Ile Arg Phe Ile
115 120 125

Asn Asp Ile Leu Leu Ser Ala Pro Ser Ile Val Ile Gly Leu Phe Val
130 135 140

Tyr Ala Ile Val Val Ala Lys Ser Gly Arg Phe Ser Gly Trp Ala Gly
145 150 155 160

Val Ile Ala Leu Ala Leu Leu Gln Ile Pro Ile Val Ile Arg Thr Thr
165 170 175

Glu Asn Met Leu Lys Leu Val Pro Asn Ala Leu Arg Glu Ala Ala Val
180 185 190

Ala Leu Gly Thr Pro Lys Trp Arg Met Val Leu Lys Ile Thr Leu Arg
195 200 205

Ala Ser Val Gly Gly Ile Val Thr Gly Val Leu Leu Ala Val Ala Arg
210 215 220

Ile Ala Gly Glu Thr Ala Pro Leu Leu Phe Thr Ala Leu Ser Asn Gln
225 230 235 240

Phe Phe Ser Trp Asp Met Ser Gln Pro Met Ala Asn Leu Pro Val Thr
245 250 255

Ile Tyr Lys Phe Ala Met Ser Pro Phe Ala Glu Trp Gln Ser Leu Ala
260 265 270

Trp Ala Gly Val Phe Leu Ile Thr Leu Gly Val Leu Gly Leu Asn Val

```
                    275                 280                 285

Leu Ala Arg Ser Ile Phe Ser Lys Lys
            290                 295

<210> SEQ ID NO 6
<211> LENGTH: 281
<212> TYPE: PRT
<213> ORGANISM: Bradyrhizobium

<400> SEQUENCE: 6

Met Asn Pro Ile Tyr Ser Arg Arg Arg Lys Asp Ile Val Val Arg
1               5                   10                  15

Gly Leu Cys Ile Ala Ala Ala Phe Gly Val Thr Trp Leu Ala Leu
                20                  25                  30

Ile Leu Ile Thr Leu Leu Tyr Asn Gly Ile Ala Gly Leu Asn Leu Glu
            35                  40                  45

Ile Phe Val Ala Asp Thr Pro Pro Gly Ser Thr Glu Gly Gly Leu
        50                  55                  60

Arg Asn Ala Ile Val Gly Ser Ile Ile Met Thr Val Leu Gly Val Gly
65                  70                  75                  80

Ile Gly Ala Pro Leu Gly Leu Phe Ala Gly Thr Tyr Leu Ala Glu Tyr
                85                  90                  95

Gly Arg Asn Asp Arg Leu Thr Ser Val Ile Arg Phe Ile Asn Asp Ile
            100                 105                 110

Leu Leu Ser Ala Pro Ser Ile Ile Gly Leu Phe Ile Tyr Gly Ala
        115                 120                 125

Val Val Val Pro Met Arg Gly Phe Ser Ala Ile Ala Gly Ser Leu Ala
        130                 135                 140

Leu Ala Val Ile Val Ile Pro Val Val Leu Arg Thr Thr Glu Asp Met
145                 150                 155                 160

Leu Leu Leu Val Pro Asn Ala Leu Arg Glu Ala Ala Ser Ala Leu Gly
                165                 170                 175

Leu Pro Arg Ser Leu Val Ile Lys Arg Ile Ala Tyr Arg Ala Ala Arg
            180                 185                 190

Ser Gly Leu Ile Thr Gly Val Leu Leu Ala Thr Ala Arg Val Ala Gly
        195                 200                 205

Glu Thr Ala Pro Leu Leu Phe Thr Ala Leu Ser Asn Gln Phe Phe Ser
        210                 215                 220

Leu Gly Leu Asn Lys Thr Met Ala Asn Leu Pro Val Thr Ile Asn Asn
225                 230                 235                 240

Phe Val Gln Ser Pro Tyr Ala Tyr Trp Lys Gln Leu Ala Trp Ser Gly
                245                 250                 255

Ala Leu Leu Ile Thr Ile Thr Val Leu Ala Leu Asn Ile Gly Ala Arg
            260                 265                 270

Ile Leu Gly Ala Glu Arg Thr Ala Lys
        275                 280

<210> SEQ ID NO 7
<211> LENGTH: 287
<212> TYPE: PRT
<213> ORGANISM: Xylella

<400> SEQUENCE: 7

Met Ser Thr Ala Ser Gln His Leu Tyr Lys Arg Arg Arg Leu Ile Asn
1               5                   10                  15

Ala Thr Ala Ile Thr Ile Ser Cys Ile Ala Ala Leu Phe Gly Leu Phe
                20                  25                  30
```

```
Phe Leu Ile Trp Ile Leu Trp Thr Leu Ile Ser Lys Gly Leu Pro Gly
            35                  40                  45

Ile Gly Leu Asp Leu Phe Thr Lys Ile Thr Pro Pro Met Gln Lys
 50                  55                  60

Gly Gly Leu Ala Asn Ala Phe Gly Ser Ala Ile Met Cys Leu Leu
 65                  70                  75                  80

Ala Ile Val Ile Gly Thr Pro Leu Gly Ile Ala Ala Gly Thr Trp Leu
            85                  90                  95

Ala Glu Tyr Gly Asn Thr Ser Lys Thr Ser Ala Val Val Arg Phe Val
            100                 105                 110

Asn Asp Ile Leu Leu Ser Ala Pro Ser Ile Val Leu Gly Leu Phe Val
            115                 120                 125

Tyr Thr Leu Tyr Val Met His Thr Gly Gly His Phe Ser Ala Phe Ser
            130                 135                 140

Gly Ala Leu Ala Leu Val Phe Ile Val Leu Pro Ile Val Val Arg Thr
145                 150                 155                 160

Thr Asp Glu Met Leu Arg Leu Val Pro Gly Gln Met Arg Glu Ala Ala
                    165                 170                 175

Leu Ser Leu Gly Ile Pro Gln Trp Lys Met Ile Ile Gln Val Leu Tyr
                180                 185                 190

Arg Ser Ala Ser Ala Gly Ile Leu Thr Gly Ile Leu Leu Ala Leu Ala
                195                 200                 205

Arg Ile Ser Gly Glu Thr Ala Pro Leu Leu Phe Thr Ala Phe Gly Asn
                210                 215                 220

Gln Tyr Trp Ser Ser Asn Ile Phe Gln Pro Ile Ala Ser Leu Pro Leu
225                 230                 235                 240

Val Met Asn Gln Phe Ala Ser Ser Pro Tyr Lys Ser Trp Gln Leu Leu
                    245                 250                 255

Ala Trp Ser Gly Ala Leu Val Leu Thr Val Phe Val Leu Leu Val Ser
                260                 265                 270

Leu Gly Ala Arg Thr Leu Leu Leu Arg Asn Lys Ile Pro Asn Glu
            275                 280                 285

<210> SEQ ID NO 8
<211> LENGTH: 304
<212> TYPE: PRT
<213> ORGANISM: Myco.pstA-1

<400> SEQUENCE: 8

Met Ser Pro Ser Thr Ser Ile Glu Ala Leu Asp Gln Pro Val Lys Pro
 1               5                  10                  15

Val Val Phe Arg Pro Leu Thr Leu Arg Arg Ile Lys Asn Ser Val
                20                  25                  30

Ala Thr Thr Phe Phe Phe Thr Ser Phe Val Val Ala Leu Ile Pro Leu
            35                  40                  45

Val Trp Leu Leu Trp Val Val Ile Ala Arg Gly Trp Phe Ala Val Thr
 50                  55                  60

Arg Ser Gly Trp Trp Thr His Ser Leu Arg Gly Val Leu Pro Glu Gln
65                  70                  75                  80

Phe Ala Gly Gly Val Tyr His Ala Leu Tyr Gly Thr Leu Val Gln Ala
                85                  90                  95

Gly Val Ala Ala Val Leu Ala Val Pro Leu Gly Leu Met Thr Ala Val
            100                 105                 110

Tyr Leu Val Glu Tyr Gly Thr Gly Arg Met Ser Arg Val Thr Thr Phe
            115                 120                 125
```

```
Thr Val Asp Val Leu Ala Gly Val Pro Ser Ile Val Ala Ala Leu Phe
    130                 135                 140

Val Phe Ser Leu Trp Ile Ala Thr Leu Gly Phe Gln Gln Ser Ala Phe
145                 150                 155                 160

Ala Val Ala Leu Ala Leu Val Leu Leu Met Leu Pro Val Val Arg
                165                 170                 175

Ala Gly Glu Glu Met Leu Arg Leu Val Pro Asp Glu Leu Arg Glu Ala
            180                 185                 190

Ser Tyr Ala Leu Gly Val Pro Lys Trp Lys Thr Ile Val Arg Ile Val
            195                 200                 205

Ala Pro Ile Ala Met Pro Gly Ile Val Ser Gly Ile Leu Leu Ser Ile
        210                 215                 220

Ala Arg Val Val Gly Glu Thr Ala Pro Val Leu Val Leu Val Gly Tyr
225                 230                 235                 240

Ser His Ser Ile Asn Leu Asp Val Phe His Gly Asn Met Ala Ser Leu
                245                 250                 255

Pro Leu Leu Ile Tyr Thr Glu Leu Thr Asn Pro Glu His Ala Gly Phe
            260                 265                 270

Leu Arg Val Trp Gly Ala Ala Leu Thr Leu Ile Ile Val Val Ala Thr
            275                 280                 285

Ile Asn Leu Ala Ala Ala Met Ile Arg Phe Val Ala Thr Arg Arg
290                 295                 300

<210> SEQ ID NO 9
<211> LENGTH: 486
<212> TYPE: PRT
<213> ORGANISM: Azotobacter

<400> SEQUENCE: 9

Val Glu Ala Glu Val Pro Arg Ala Arg Leu Ala Ala Ser Gly Leu
1               5                   10                  15

Pro Val Asp Ala Asp Gly Gly Glu Phe Met Thr Arg Glu Leu Leu Lys
            20                  25                  30

Val Gly Asn Arg Glu Leu Phe Gly Ala Asp Phe Asn Trp Val Val Gly
        35                  40                  45

Glu Trp Leu Ala Asn Pro Arg Lys Pro Glu Ser Leu Val Val Phe Glu
50                  55                  60

Arg Arg Glu Trp Gly Asn Phe Tyr Gly Tyr Leu Leu Gly Val Lys Glu
65                  70                  75                  80

Ser Gly Arg Leu Val Ala Glu Gly Glu Gly Ala Trp Lys Glu Leu Leu
                85                  90                  95

Ser Arg Ile Glu Arg Val Ala Gly Leu His Glu Gln Leu Ala Gln Leu
            100                 105                 110

Glu Arg Ala Asp Ile Gly Arg Val Asn His Ala Leu Glu Arg Leu Arg
        115                 120                 125

Leu Lys Glu Arg Gly Leu Glu Leu Gly Gly Asp Leu Asp Ala Asp Ala
130                 135                 140

Gln Ala Asp Leu Ala Ala Glu Arg Ala Gln Trp Gly Val Arg Tyr Arg
145                 150                 155                 160

Glu Leu Glu Ser Gln Leu Val Val Leu Gln Gln Glu Phe Asn Arg Asp
                165                 170                 175

Ser Val Leu Val Arg Thr Ala Asp Gly Arg Glu Glu Glu Ile Thr Leu
            180                 185                 190

Gly Lys Val Val Arg Ala Tyr Gln Pro Asn Ala Met Gly Leu Gly Glu
        195                 200                 205
```

Lys Phe Gly Phe Tyr Phe Ala Lys Leu Trp Glu Phe Val Ser Asp Glu
    210                 215                 220

Pro Arg Glu Ala Asn Thr Glu Gly Ile Phe Pro Ala Ile Phe Gly
225                 230                 235                 240

Thr Val Met Met Thr Leu Ile Met Ala Val Leu Val Thr Pro Phe Gly
            245                 250                 255

Val Leu Ala Ala Ile Tyr Leu Arg Glu Tyr Ala Lys Gln Gly Pro Leu
            260                 265                 270

Thr Arg Val Ile Arg Ile Ala Val Asn Asn Leu Ala Gly Val Pro Ala
            275                 280                 285

Ile Val Tyr Gly Val Phe Gly Leu Gly Phe Phe Val Tyr Val Leu Gly
    290                 295                 300

Gly Ser Ile Asp Arg Leu Leu Phe Ala Glu Ala Leu Pro Ala Pro Thr
305                 310                 315                 320

Phe Gly Thr Pro Gly Leu Leu Trp Ala Ser Leu Thr Leu Ala Ile Leu
            325                 330                 335

Ala Val Pro Val Val Ile Val Ala Thr Glu Glu Gly Leu Ala Arg Ile
            340                 345                 350

Pro Arg Ala Leu Arg Glu Gly Ser Leu Ala Leu Gly Ala Thr Lys Ala
            355                 360                 365

Glu Thr Leu Trp Lys Val Val Leu Pro Met Ala Ser Pro Ala Met Met
    370                 375                 380

Thr Gly Leu Ile Leu Ala Val Ala Arg Ala Ala Gly Glu Val Ala Pro
385                 390                 395                 400

Leu Met Leu Val Gly Val Val Lys Leu Ala Pro Ser Leu Pro Val Asp
            405                 410                 415

Gly Asn Tyr Pro Tyr Leu His Leu Asp Gln Lys Ile Met His Leu Gly
            420                 425                 430

Phe His Ile Tyr Asp Val Gly Phe Gln Ser Pro Asn Val Glu Ala Ala
    435                 440                 445

Arg Pro Leu Val Tyr Ala Thr Ala Leu Leu Leu Val Leu Val Ile Ala
    450                 455                 460

Leu Leu Asn Leu Ser Ala Val Tyr Ile Arg Asn Arg Leu Arg Glu Lys
465                 470                 475                 480

Tyr Lys Ala Leu Asp His
                485

<210> SEQ ID NO 10
<211> LENGTH: 291
<212> TYPE: PRT
<213> ORGANISM: Bacteroides

<400> SEQUENCE: 10

Met Glu Ile Leu Asn Asn Thr Lys Ala Lys Arg Arg Ser Gln Gly Ile
1               5                   10                  15

Ala Phe Gly Ile Phe Arg Leu Leu Ser Leu Cys Ile Val Leu Ile Leu
            20                  25                  30

Phe Ala Ile Leu Gly Phe Ile Ile Tyr Lys Gly Ile Gly Val Ile Ser
        35                  40                  45

Trp Asp Phe Leu Thr Thr Ala Pro Thr Asp Gly Met Thr Gly Gly Gly
    50                  55                  60

Ile Trp Pro Ala Ile Val Gly Thr Phe Tyr Leu Met Val Gly Ser Ala
65                  70                  75                  80

Leu Phe Ala Phe Pro Val Gly Val Met Ser Gly Ile Tyr Met Asn Glu
            85                  90                  95

```
Tyr Ala Pro Lys Gly Lys Leu Val Arg Phe Ile Arg Val Met Thr Asn
                100                 105                 110

Asn Leu Ser Gly Ile Pro Ser Ile Val Phe Gly Leu Phe Gly Met Ala
            115                 120                 125

Leu Phe Val Asn Tyr Met Asp Phe Gly Asp Ser Ile Leu Ala Gly Ser
130                 135                 140

Leu Thr Leu Gly Leu Leu Cys Val Pro Leu Val Ile Arg Thr Thr Glu
145                 150                 155                 160

Glu Ala Leu Lys Ala Ile Pro Asp Ser Met Arg Glu Gly Ser Arg Ala
                165                 170                 175

Leu Gly Ala Thr Lys Leu Gln Thr Ile Trp His Val Ile Leu Pro Met
            180                 185                 190

Gly Met Pro Asn Ile Ile Thr Gly Leu Ile Leu Ala Leu Gly Arg Val
            195                 200                 205

Ser Gly Glu Thr Ala Pro Ile Leu Phe Thr Cys Ala Ala Tyr Phe Leu
        210                 215                 220

Pro Gln Leu Pro Thr Ser Ile Leu Asp Gln Cys Met Ala Leu Pro Tyr
225                 230                 235                 240

His Leu Tyr Val Ile Ser Thr Ser Gly Thr Asp Met Glu Ala Gln Leu
                245                 250                 255

Pro Leu Ala Tyr Gly Thr Ala Leu Val Leu Ile Val Ile Ile Leu Leu
            260                 265                 270

Val Asn Leu Leu Ala Asn Ala Leu Arg Lys Tyr Phe Glu Lys Lys Val
        275                 280                 285

Lys Met Asn
    290

<210> SEQ ID NO 11
<211> LENGTH: 319
<212> TYPE: PRT
<213> ORGANISM: Salmonella

<400> SEQUENCE: 11

Met Ala Ala Thr Lys Pro Ala Phe Asn Pro Gly Lys Lys Gly Asp
1               5                   10                  15

Met Ile Phe Ser Ala Leu Val Lys Leu Ala Ala Leu Ile Val Leu Leu
                20                  25                  30

Met Leu Gly Gly Ile Ile Val Ser Leu Ile Ile Ser Ser Trp Pro Ser
            35                  40                  45

Ile Gln Lys Phe Gly Phe Ser Phe Leu Trp Thr Lys Glu Trp Asp Ala
50                  55                  60

Pro Asn Asp Ile Tyr Gly Ala Leu Val Pro Ile Tyr Gly Thr Leu Val
65                  70                  75                  80

Thr Ser Phe Ile Ala Leu Leu Ile Ala Val Pro Val Ser Phe Gly Ile
                85                  90                  95

Ala Leu Phe Leu Thr Glu Leu Ala Pro Gly Trp Leu Lys Arg Pro Leu
            100                 105                 110

Gly Ile Ala Ile Glu Leu Leu Ala Ala Ile Pro Ser Ile Val Tyr Gly
            115                 120                 125

Met Trp Gly Leu Phe Ile Phe Ala Pro Leu Phe Ala Thr Tyr Phe Gln
        130                 135                 140

Glu Pro Val Gly Asn Ile Leu Ser Asn Ile Pro Phe Val Gly Ala Leu
145                 150                 155                 160

Phe Ser Gly Pro Ala Phe Gly Ile Gly Ile Leu Ala Ala Gly Val Ile
                165                 170                 175
```

```
Leu Ala Ile Met Ile Ile Pro Tyr Ile Ala Ala Val Met Arg Asp Val
        180                 185                 190

Phe Glu Gln Thr Pro Val Met Met Lys Glu Ser Ala Tyr Gly Ile Gly
        195                 200                 205

Cys Thr Thr Trp Glu Val Ile Trp Arg Ile Val Leu Pro Phe Thr Lys
        210                 215                 220

Asn Gly Val Ile Gly Gly Ile Met Leu Gly Leu Gly Arg Ala Leu Gly
225                 230                 235                 240

Glu Thr Met Ala Val Thr Phe Ile Ile Gly Asn Thr Tyr Gln Leu Asp
        245                 250                 255

Ser Ala Ser Leu Tyr Met Pro Gly Asn Ser Ile Thr Ser Ala Leu Ala
        260                 265                 270

Asn Glu Phe Ala Glu Ala Glu Ser Gly Leu His Val Ala Ala Leu Met
        275                 280                 285

Glu Leu Gly Leu Ile Leu Phe Val Ile Thr Phe Ile Val Leu Ala Ala
        290                 295                 300

Ser Lys Phe Met Ile Met Arg Leu Ala Lys Asn Glu Gly Ala Arg
305                 310                 315

<210> SEQ ID NO 12
<211> LENGTH: 320
<212> TYPE: PRT
<213> ORGANISM: Pasteurella

<400> SEQUENCE: 12

Met Leu Arg Arg Lys Thr Gln Ala Glu Thr Asn Arg Leu Asn His His
1               5                   10                  15

Ile Ile Glu Leu Leu Phe Arg Gln Thr Thr Arg Phe Phe Ala Ile Phe
        20                  25                  30

Val Phe Leu Leu Leu Ala Ala Val Met Thr Ser Leu Val Phe Gly Ser
        35                  40                  45

Trp Asp Ser Phe Ser Thr Phe Gly Phe Ser Phe Leu Trp His Asn Asp
        50                  55                  60

Trp Asn Pro Val Gln Glu Ser Tyr Gly Ala Ile Ile Pro Ile Val Gly
65              70                  75                  80

Thr Leu Ile Thr Ser Phe Leu Ala Leu Ile Ile Ala Val Pro Ile Ser
        85                  90                  95

Phe Gly Ile Ala Ile Phe Leu Thr Glu Leu Ala Pro Glu Trp Leu Arg
        100                 105                 110

Arg Pro Val Gly Thr Ala Ile Glu Met Leu Ala Ala Ile Pro Ser Ile
        115                 120                 125

Ile Tyr Gly Met Trp Gly Leu Phe Ile Phe Val Pro Leu Phe Gln Glu
        130                 135                 140

His Ile Gln Pro Ser Leu Ile Glu Trp Phe Gly Asp Leu Pro Val Phe
145             150                 155                 160

Ser Tyr Leu Phe Ser Gly Ala Pro Phe Gly Ile Gly Leu Phe Thr Ala
        165                 170                 175

Gly Leu Val Leu Ala Ile Met Ile Ile Pro Phe Ile Ala Ala Val Met
        180                 185                 190

Arg Asp Val Phe Thr Ile Val Pro Ala Ile Leu Lys Glu Ser Ala Tyr
        195                 200                 205

Gly Leu Gly Ser Thr Thr Trp Glu Val Met Trp Lys Val Val Leu Pro
        210                 215                 220

Tyr Thr Lys Thr Gly Val Val Gly Gly Ile Met Leu Gly Leu Gly Arg
225             230                 235                 240
```

```
Ala Leu Gly Glu Thr Met Ala Val Thr Phe Val Ile Gly Asn Ala Phe
            245                 250                 255

His Leu Pro Glu Ser Leu Phe Ser Pro Ser Thr Ser Ile Ala Ser Ala
            260                 265                 270

Ile Ala Asn Glu Phe Asn Glu Ala Ser Gly Leu Gln Lys Ser Ala Leu
            275                 280                 285

Met Glu Leu Gly Leu Ile Leu Phe Leu Ile Thr Thr Val Val Leu Ser
            290                 295                 300

Ile Ser Arg Leu Leu Ile Met Arg Ile Glu Lys Lys Glu Gly Arg Lys
305                 310                 315                 320

<210> SEQ ID NO 13
<211> LENGTH: 338
<212> TYPE: PRT
<213> ORGANISM: Myco.pstC-1

<400> SEQUENCE: 13

Met Leu Ala Arg Ala Gly Glu Val Gly Arg Ala Gly Pro Ala Ile Arg
1               5                   10                  15

Trp Leu Gly Gly Ile Gly Ala Val Ile Pro Leu Leu Ala Leu Val Leu
            20                  25                  30

Val Leu Val Val Leu Val Ile Glu Ala Met Gly Ala Ile Arg Leu Asn
            35                  40                  45

Gly Leu His Phe Phe Thr Ala Thr Glu Trp Asn Pro Gly Asn Thr Tyr
        50                  55                  60

Gly Glu Thr Val Val Thr Asp Gly Val Ala His Pro Val Gly Ala Tyr
65                  70                  75                  80

Tyr Gly Ala Leu Pro Leu Ile Val Gly Thr Leu Ala Thr Ser Ala Ile
                85                  90                  95

Ala Leu Ile Ile Ala Val Pro Val Ser Val Gly Ala Ala Leu Val Ile
            100                 105                 110

Val Glu Arg Leu Pro Lys Arg Leu Ala Glu Ala Val Gly Ile Val Leu
            115                 120                 125

Glu Leu Leu Ala Gly Ile Pro Ser Val Val Gly Leu Trp Gly Ala
        130                 135                 140

Met Thr Phe Gly Pro Phe Ile Ala His His Ile Ala Pro Val Ile Ala
145                 150                 155                 160

His Asn Ala Pro Asp Val Pro Val Leu Asn Tyr Leu Arg Gly Asp Pro
                165                 170                 175

Gly Asn Gly Glu Gly Met Leu Val Ser Gly Leu Val Leu Ala Val Met
            180                 185                 190

Val Val Pro Ile Ile Ala Thr Thr Thr His Asp Leu Phe Arg Gln Val
            195                 200                 205

Pro Val Leu Pro Arg Glu Gly Ala Ile Ala Leu Gly Met Ser Asn Trp
        210                 215                 220

Glu Cys Val Arg Arg Val Thr Leu Pro Trp Val Ser Ser Gly Ile Val
225                 230                 235                 240

Gly Ala Val Val Leu Gly Leu Gly Arg Ala Leu Gly Glu Thr Met Ala
                245                 250                 255

Val Ala Met Val Ser Gly Ala Val Leu Gly Ala Met Pro Ala Asn Ile
            260                 265                 270

Tyr Ala Thr Met Thr Thr Ile Ala Ala Thr Ile Val Ser Gln Leu Asp
            275                 280                 285

Ser Ala Met Thr Asp Ser Thr Asn Phe Ala Val Lys Thr Leu Ala Glu
            290                 295                 300
```

```
Val Gly Leu Val Leu Met Val Ile Thr Leu Leu Thr Asn Val Ala Ala
305                 310                 315                 320

Arg Gly Met Val Arg Arg Val Ser Arg Thr Ala Leu Pro Val Gly Arg
                325                 330                 335

Gly Ile

<210> SEQ ID NO 14
<211> LENGTH: 324
<212> TYPE: PRT
<213> ORGANISM: Myco.pstC-2

<400> SEQUENCE: 14

Met Val Thr Glu Pro Leu Thr Lys Pro Ala Leu Val Ala Val Asp Met
1               5                   10                  15

Arg Pro Ala Arg Arg Gly Glu Arg Leu Phe Lys Leu Ala Ala Ser Ala
            20                  25                  30

Ala Gly Ser Thr Ile Val Ile Ala Ile Leu Leu Ile Ala Ile Phe Leu
        35                  40                  45

Leu Val Arg Ala Val Pro Ser Leu Arg Ala Asn His Ala Asn Phe Phe
50                  55                  60

Thr Ser Thr Gln Phe Asp Thr Ser Asp Asp Glu Gln Leu Ala Phe Gly
65                  70                  75                  80

Val Arg Asp Leu Phe Met Val Thr Ala Leu Ser Ser Ile Thr Ala Leu
                85                  90                  95

Val Leu Ala Val Pro Val Ala Val Gly Ile Ala Val Phe Leu Thr His
            100                 105                 110

Tyr Ala Pro Arg Arg Leu Ser Arg Pro Phe Gly Ala Met Val Asp Leu
        115                 120                 125

Leu Ala Ala Val Pro Ser Ile Ile Phe Gly Leu Trp Gly Ile Phe Val
130                 135                 140

Leu Ala Pro Lys Leu Glu Pro Ile Ala Arg Phe Leu Asn Arg Asn Leu
145                 150                 155                 160

Gly Trp Leu Phe Leu Phe Lys Gln Gly Asn Val Ser Leu Ala Gly Gly
                165                 170                 175

Gly Thr Ile Phe Thr Ala Gly Ile Val Leu Ser Val Met Ile Leu Pro
            180                 185                 190

Ile Val Thr Ser Ile Ser Arg Glu Val Phe Arg Gln Thr Pro Leu Ile
        195                 200                 205

Gln Ile Glu Ala Ala Leu Ala Leu Gly Ala Thr Lys Trp Glu Val Val
210                 215                 220

Arg Met Thr Val Leu Pro Tyr Gly Arg Ser Gly Val Val Ala Ala Ser
225                 230                 235                 240

Met Leu Gly Leu Gly Arg Ala Leu Gly Glu Thr Val Ala Val Leu Val
                245                 250                 255

Ile Leu Arg Ser Ala Ala Arg Pro Gly Thr Trp Ser Leu Phe Asp Gly
            260                 265                 270

Gly Tyr Thr Phe Ala Ser Lys Ile Ala Ser Ala Ser Glu Phe Ser
        275                 280                 285

Glu Pro Leu Pro Thr Gly Ala Tyr Ile Ser Ala Gly Phe Ala Leu Phe
290                 295                 300

Val Leu Thr Phe Leu Val Asn Ala Ala Ala Arg Ala Ile Ala Gly Gly
305                 310                 315                 320

Lys Val Asn Gly
```

<210> SEQ ID NO 15
<211> LENGTH: 346
<212> TYPE: PRT
<213> ORGANISM: E.coli

<400> SEQUENCE: 15

Met Lys Val Met Arg Thr Thr Val Ala Thr Val Ala Ala Thr Leu
1               5                   10                  15

Ser Met Ser Ala Phe Ser Val Phe Ala Glu Ala Ser Leu Thr Gly Ala
            20                  25                  30

Gly Ala Thr Phe Pro Ala Pro Val Tyr Ala Lys Trp Ala Asp Thr Tyr
        35                  40                  45

Gln Lys Glu Thr Gly Asn Lys Val Asn Tyr Gln Gly Ile Gly Ser Ser
    50                  55                  60

Gly Gly Val Lys Gln Ile Ile Ala Asn Thr Val Asp Phe Gly Ala Ser
65                  70                  75                  80

Asp Ala Pro Leu Ser Asp Glu Lys Leu Ala Gln Glu Gly Leu Phe Gln
                85                  90                  95

Phe Pro Thr Val Ile Gly Gly Val Val Leu Ala Val Asn Ile Pro Gly
            100                 105                 110

Leu Lys Ser Gly Glu Leu Val Leu Asp Gly Lys Thr Leu Gly Asp Ile
        115                 120                 125

Tyr Leu Gly Lys Ile Lys Lys Trp Asp Asp Glu Ala Ile Ala Lys Leu
    130                 135                 140

Asn Pro Gly Leu Lys Leu Pro Ser Gln Asn Ile Ala Val Val Arg Arg
145                 150                 155                 160

Ala Asp Gly Ser Gly Thr Ser Phe Val Phe Thr Ser Tyr Leu Ala Lys
                165                 170                 175

Val Asn Glu Glu Trp Lys Asn Asn Val Gly Thr Gly Ser Thr Val Lys
            180                 185                 190

Trp Pro Ile Gly Leu Gly Gly Lys Gly Asn Asp Gly Ile Ala Ala Phe
        195                 200                 205

Val Gln Arg Leu Pro Gly Ala Ile Gly Tyr Val Glu Tyr Ala Tyr Ala
    210                 215                 220

Lys Gln Asn Asn Leu Ala Tyr Thr Lys Leu Ile Ser Ala Asp Gly Lys
225                 230                 235                 240

Pro Val Ser Pro Thr Glu Glu Asn Phe Ala Cys Ala Ala Lys Gly Ala
                245                 250                 255

Asp Trp Ser Lys Thr Phe Ala Gln Asp Leu Thr Asn Gln Lys Gly Glu
            260                 265                 270

Asp Ala Trp Pro Ile Thr Ser Thr Thr Phe Ile Leu Ile His Lys Asp
        275                 280                 285

Gln Lys Lys Pro Glu Gln Gly Thr Glu Val Leu Lys Phe Phe Asp Trp
    290                 295                 300

Ala Tyr Lys Thr Gly Ala Lys Gln Ala Asn Asp Leu Asp Tyr Ala Ser
305                 310                 315                 320

Leu Pro Asp Cys Val Val Glu Gln Val Arg Ala Ala Trp Lys Thr Asn
                325                 330                 335

Ile Lys Asp Ser Ser Gly Lys Pro Leu Tyr
            340                 345

<210> SEQ ID NO 16
<211> LENGTH: 346
<212> TYPE: PRT
<213> ORGANISM: Erwinia

<400> SEQUENCE: 16

```
Met Thr Ser Met His Lys Thr Leu Ala Gln Cys Val Ala Leu Thr Leu
1               5                   10                  15
Ser Leu Ser Ala Val Ser Ala Leu Ala Ala Thr Asn Leu Thr Gly Ala
            20                  25                  30
Gly Gly Thr Phe Pro Ala Pro Val Tyr Asn Lys Trp Ala Ala Glu Tyr
            35                  40                  45
His Thr Ala Thr Gly Ser Gln Val Asn Tyr Gln Gly Ile Gly Ser Ser
50                  55                  60
Gly Gly Val Lys Gln Ile Ile Ala Lys Thr Ala Asp Phe Gly Ala Ser
65                  70                  75                  80
Asp Ala Pro Met Lys Asp Glu Asp Leu Ala Lys Asn Gly Leu Phe Gln
                85                  90                  95
Phe Pro Thr Val Ile Gly Gly Val Val Leu Ala Val Asn Ile Pro Gly
            100                 105                 110
Ile Lys Ser Gly Glu Leu Thr Leu Asp Gly Lys Thr Val Gly Asp Ile
            115                 120                 125
Tyr Leu Gly Thr Val Lys Lys Trp Asn Asp Pro Ala Ile Thr Lys Leu
130                 135                 140
Asn Pro Gly Val Lys Leu Pro Asp Ala Asn Ile Asn Val Val Arg Arg
145                 150                 155                 160
Ala Asp Gly Ser Gly Thr Ser Phe Val Phe Thr Ser Tyr Leu Ser Lys
                165                 170                 175
Val Asn Lys Asp Trp Ser Ser Lys Val Gly Lys Gly Ser Thr Val Asn
            180                 185                 190
Trp Pro Val Gly Leu Gly Gly Lys Gly Asn Asp Gly Val Ala Ala Phe
            195                 200                 205
Val Gln Arg Leu Pro Gly Ser Val Gly Tyr Val Glu Tyr Ala Tyr Ala
210                 215                 220
Lys Gln Asn Ser Leu Ala Tyr Thr Lys Leu Val Asp Ala Asp Gly Lys
225                 230                 235                 240
Ala Ile Ala Pro Ser Glu Lys Ser Phe Ser Asp Ala Ala Lys Gly Ala
                245                 250                 255
Asp Trp Ser Thr Ser Phe Ala Gln Asp Leu Thr Phe Gln Lys Gly Asp
            260                 265                 270
Asn Ala Trp Pro Ile Thr Ser Thr Phe Ile Leu Val His Lys Glu
            275                 280                 285
Gln Ala Asn Thr Ala Lys Gly Ala Ala Val Leu Gln Phe Phe Asp Trp
290                 295                 300
Ala Tyr Lys Asn Gly Gly Lys Thr Thr Ser Ala Leu Asp Tyr Ala Ser
305                 310                 315                 320
Leu Pro Ala Pro Val Val Glu Gln Ile Arg Ala Ala Trp Lys Ser Asn
                325                 330                 335
Val Lys Asp Ser Ser Gly Lys Ala Leu Tyr
            340                 345

<210> SEQ ID NO 17
<211> LENGTH: 363
<212> TYPE: PRT
<213> ORGANISM: Xanthomonas

<400> SEQUENCE: 17

Met Arg Arg Thr Pro Leu Pro Cys Asn Gly Val Leu Arg Asp Val Ile
1               5                   10                  15
Pro Ile Ala Thr Arg Ser Cys Ser Val Ile Ser Ser Ile Lys Ser Arg
            20                  25                  30
```

```
Leu Ala Val Gly Val Leu Ala Ala Leu Ala Met Gly Ala Gln Ala
        35                  40                  45

Ala Asp Val Thr Gly Ala Gly Ala Ser Phe Ile Tyr Pro Val Met Ser
 50                  55                  60

Lys Trp Ser Ala Asp Tyr Asn Thr Ala Thr Lys Lys Gln Val Asn Tyr
 65                  70                  75                  80

Gln Ser Ile Gly Ser Gly Gly Ile Ala Gln Ile Lys Ala Ala Ser
                 85                  90                  95

Val Asp Phe Gly Ser Ser Asp Ala Pro Leu Lys Pro Glu Glu Leu Ala
                100                 105                 110

Ala Ala Gly Leu Ala Gln Phe Pro Ser Val Ile Gly Gly Val Val Pro
            115                 120                 125

Val Ile Asn Val Pro Gly Ile Ala Ala Gly Ala Val Lys Leu Asp Gly
            130                 135                 140

Lys Thr Leu Gly Asp Ile Phe Leu Gly Lys Val Thr Thr Trp Asn Asp
145                 150                 155                 160

Ala Ala Ile Val Ala Leu Asn Pro Gly Val Lys Leu Pro Asp Ser Lys
                165                 170                 175

Ile Thr Val Val His Arg Ser Asp Gly Ser Gly Thr Ser Phe Asn Phe
                180                 185                 190

Thr Asn Tyr Leu Ser Lys Val Asn Pro Asp Trp Lys Ser Lys Val Gly
                195                 200                 205

Glu Gly Thr Ala Val Gln Trp Pro Thr Gly Ile Gly Gly Lys Gly Asn
            210                 215                 220

Glu Gly Val Ala Ala Tyr Val Lys Gln Ile Lys Gly Gly Ile Gly Tyr
225                 230                 235                 240

Val Glu Leu Ser Tyr Ala Leu Gln Asn Lys Met Ala Tyr Thr Ala Met
                245                 250                 255

Lys Asn Ala Ala Gly Lys Phe Val Gln Pro Ser Asp Glu Thr Phe Ala
                260                 265                 270

Ala Ala Ala Asn Ser Ala Asp Trp Gly Ser Ser Lys Asp Phe Tyr Leu
            275                 280                 285

Val Met Thr Asn Ala Ala Gly Asp Asn Ala Trp Pro Ile Thr Ala Thr
            290                 295                 300

Asn Phe Ile Leu Val Gln Lys Lys Pro Lys Asn Pro Ala Gly Leu Lys
305                 310                 315                 320

Asn Thr Leu Glu Phe Phe Arg Trp Val Tyr Ser Lys Gly Asp Ala Gln
                325                 330                 335

Ala Lys Ala Leu Asp Tyr Val Pro Leu Pro Asp Thr Leu Val Ser Gln
                340                 345                 350

Ile Glu Ala Tyr Trp Ala Lys Thr Leu Pro Arg
                355                 360

<210> SEQ ID NO 18
<211> LENGTH: 361
<212> TYPE: PRT
<213> ORGANISM: limicola

<400> SEQUENCE: 18

Met Arg Cys Gln Leu Ile Met Ile Phe Met Phe His Thr Phe Asn Arg
 1               5                  10                  15

Tyr Pro Ile Met Met Ile Lys Arg Phe Trp Lys Thr Ala Phe Met Ala
                20                  25                  30

Cys Ala Phe Ala Gly Leu Ala Thr Gly Ser Ala Glu Ala Arg Glu Gln
            35                  40                  45
```

```
Ile Arg Ile Val Gly Ser Ser Thr Val Phe Pro Phe Ala Ser Tyr Val
 50                  55                  60

Ala Glu Glu Phe Gly Lys Thr Thr Lys Phe Ala Thr Pro Val Ile Glu
 65                  70                  75                  80

Ser Thr Gly Ser Gly Gly Gly His Lys Leu Phe Gly Glu Gly Asp Gly
                 85                  90                  95

Leu Ala Thr Pro Asp Ile Thr Asn Ser Ser Arg Arg Met Lys Lys Ser
            100                 105                 110

Glu Phe Glu Arg Ala Gln Gln Asn Gly Val Lys Thr Ile His Glu Ala
        115                 120                 125

Val Ile Gly Tyr Asp Gly Ile Val Ala Asn Ala Lys Ala Ala Pro
130                 135                 140

Ala Leu Lys Leu Ser Arg Lys Asp Ile Phe Met Ala Leu Ala Glu Glu
145                 150                 155                 160

Val Pro Val Lys Gly Gln Leu Val Lys Asn Pro Tyr Lys Met Trp Asn
                165                 170                 175

Gln Ile Asn Pro Ala Leu Pro Lys Gln Lys Ile Leu Val Tyr Gly Pro
            180                 185                 190

Pro Thr Ser Ser Gly Thr Arg Asp Ala Phe Asp Glu Met Val Met Glu
        195                 200                 205

Ala Ala Ser Lys Lys Met Thr Glu Tyr Gly Thr Ala Ala Gly Lys Tyr
210                 215                 220

Lys Lys Ile Arg Gln Asp Gly Val Tyr Val Pro Ser Gly Glu Asn Asp
225                 230                 235                 240

Asn Leu Ile Val Gln Arg Ile Val Lys Asp Arg Asn Ala Val Gly Val
                245                 250                 255

Phe Gly Tyr Ser Phe Leu Glu Glu Asn Ala Asp Arg Ile Lys Gly Ala
            260                 265                 270

Thr Val Asp Gly Val Ala Pro Leu Pro Ala Asn Ile Thr Thr Gly Lys
        275                 280                 285

Tyr Pro Val Ser Arg Asp Leu Phe Phe Tyr Val Lys Gly Ser His Leu
290                 295                 300

Ala Gln Val Lys Gly Leu Lys Glu Tyr Val Asp Leu Phe Leu Gly Glu
305                 310                 315                 320

Lys Met Ile Gly Asp Tyr Gly Tyr Leu Lys Lys Ile Gly Leu Ile Pro
                325                 330                 335

Leu Pro Lys Ala Lys Arg Asp Ala Val Arg Ala Ser Trp Thr Ala Lys
            340                 345                 350

Lys Val Leu Ser Ala Ala Ser Leu Asp
        355                 360

<210> SEQ ID NO 19
<211> LENGTH: 341
<212> TYPE: PRT
<213> ORGANISM: Chromohalobacter

<400> SEQUENCE: 19

Met Asn Arg Ile Leu Lys Thr Thr Ala Leu Ala Ala Val Met Ser
 1               5                  10                  15

Val Ala Gly Val Ala Gln Ala Gln Asp Glu Thr Arg Glu Gln Leu Arg
                 20                  25                  30

Ile Val Gly Ser Ser Thr Val Tyr Pro Phe Ala Ser Tyr Val Val Glu
            35                  40                  45

Glu Phe Gly Ala Thr Thr Asp Tyr Pro Thr Pro Val Ile Glu Ser Thr
        50                  55                  60
```

```
Gly Ser Gly Gly Gly Leu Arg Leu Phe Cys Asn Gly Val Gly Leu Asp
65                  70                  75                  80

Thr Pro Asp Ile Thr Asn Ala Ser Arg Arg Met Lys Pro Ser Glu Phe
                85                  90                  95

Glu Arg Cys Gln Glu Asn Gly Val Thr Asp Ile Thr Glu Ala Lys Ile
            100                 105                 110

Gly Tyr Asp Gly Ile Ala Phe Ala Glu Ser Asn Thr Asn Glu Pro Val
        115                 120                 125

Asn Phe Thr Arg Glu Gln Leu Phe Leu Ala Leu Ala Ala Lys Val Pro
    130                 135                 140

Gln Asp Gly Glu Leu Val Asp Asn Pro Tyr Thr Lys Trp Ser Asp Ile
145                 150                 155                 160

Asp Ser Ser Leu Pro Asp Arg Glu Ile Met Val Tyr Gly Pro Pro Thr
                165                 170                 175

Thr Ser Gly Thr Arg Asp Ala Phe Glu Glu Leu Val Met Glu Ala Ala
                180                 185                 190

Ser Glu Glu Met Asp Ala Tyr Gly Gly Glu Gly Tyr Thr Asp Ile Arg
            195                 200                 205

Gln Asp Gly Pro Tyr Val Asp Ala Gly Glu Asn Asp Asn Leu Ile Val
210                 215                 220

Gln Arg Leu Gln Glu Asn Thr Thr Ala Phe Gly Ile Phe Gly Tyr Ser
225                 230                 235                 240

Phe Leu Glu Glu Asn Ala Asp Ser Leu Thr Ala Ala Ser Ile Asp Gly
                245                 250                 255

Val Glu Pro Glu Pro Glu Ala Ile Ser Ser Gly Glu Tyr Pro Val Ser
                260                 265                 270

Arg Ser Leu Phe Phe Tyr Val Lys Asn Gln His Ala Asp Ser Val Pro
            275                 280                 285

Ala Met Tyr Pro Tyr Val Asp Leu Phe Met Ser Glu Gln Met Ile Ser
        290                 295                 300

Pro Met Gly Tyr Leu Lys Gly Leu Gly Leu Ile Pro Leu Pro Glu Asp
305                 310                 315                 320

Ala Arg Glu Gln Ala Arg Ser Asp Val Glu Asn Arg Glu Ser Leu Glu
                325                 330                 335

Leu Ser Asp Leu Lys
            340

<210> SEQ ID NO 20
<211> LENGTH: 377
<212> TYPE: PRT
<213> ORGANISM: phaeobacteroides

<400> SEQUENCE: 20

Met Thr Lys Thr Tyr Ser Met Thr Ala Leu Leu Leu Met Leu Ala Gly
1               5                   10                  15

Phe Leu Ser Val Val Gly Cys Gly Pro Lys Ala Asp Gln Ala Ala Lys
                20                  25                  30

Asp Gly Gln Ala Ala Ser Glu Thr Glu Gln Thr Gly Glu Ala Ile Glu
            35                  40                  45

Ser Ala Arg Asp Tyr Ile Ser Val Val Gly Ser Ser Thr Val Tyr Pro
        50                  55                  60

Phe Ala Thr Val Val Ala Glu Gln Phe Gly Lys Thr Ser Asp Phe Lys
65                  70                  75                  80

Thr Pro Lys Ile Glu Ser Thr Gly Ser Gly Gly Gly Phe Lys Leu Phe
                85                  90                  95
```

Ala Ala Gly Val Gly Val Glu His Pro Asp Ile Thr Asn Ala Ser Arg
            100                 105                 110

Arg Ile Lys Lys Ser Glu Cys Glu Met Cys Ala Glu Asn Gly Val Ser
        115                 120                 125

Glu Val Val Glu Leu Lys Ile Gly Tyr Asp Gly Ile Val Met Ala Asn
    130                 135                 140

Ser Lys Lys Ala Glu Pro Phe Lys Val Ser Arg Lys Asp Ile Phe Leu
145                 150                 155                 160

Ala Leu Ala Lys Glu Val Pro Asp Pro Asn Gly Glu Asp Gly Thr Leu
                165                 170                 175

Val Ala Asn Pro Tyr Thr Thr Trp Lys Glu Val Asn Pro Glu Leu Pro
            180                 185                 190

Glu Val Lys Ile Glu Val Leu Gly Pro Pro Thr Ser Gly Thr Arg
        195                 200                 205

Asp Ala Phe Val Glu Leu Ala Met Glu Ala Gly Ala Lys Glu Phe Ala
    210                 215                 220

Trp Ile Lys Ala Leu Lys Lys Glu Asp Lys Asp Lys Phe Lys Gln Ile
225                 230                 235                 240

Ser His Thr Val Arg Glu Asp Gly Ala Tyr Val Glu Ala Gly Glu Asn
                245                 250                 255

Asp Asn Leu Ile Val Gln Lys Leu Asp Ala Asn Pro Asp Ala Leu Gly
            260                 265                 270

Val Phe Gly Phe Ser Phe Leu Asp Gln Asn Lys Asp Lys Val Gln Gly
        275                 280                 285

Ser Phe Val Asp Gly Val Glu Pro Ala Phe Ser Ala Ile Ala Asp Gly
    290                 295                 300

Ser Tyr Pro Leu Ser Arg Pro Leu Tyr Phe Tyr Val Lys Lys Ala His
305                 310                 315                 320

Val Gly Thr Ile Pro Gly Met Gln Glu Tyr Leu Thr Glu Phe Thr Ser
                325                 330                 335

Glu Lys Ala Trp Gly Asp Glu Gly Tyr Leu Thr Glu Lys Gly Leu Ile
            340                 345                 350

Pro Met Pro Lys Glu Glu Arg Glu Lys Tyr Ala Asn Val Ala Met Glu
        355                 360                 365

Leu Ile Ala Val Ser Cys Asp Glu Leu
    370                 375

<210> SEQ ID NO 21
<211> LENGTH: 301
<212> TYPE: PRT
<213> ORGANISM: Myco.pstA-2

<400> SEQUENCE: 21

Met Gly Glu Ser Ala Glu Ser Gly Ser Arg Gln Leu Pro Ala Met Ser
1               5                   10                  15

Pro Pro Arg Arg Ser Val Ala Tyr Arg Arg Lys Ile Val Asp Ala Leu
            20                  25                  30

Trp Trp Ala Ala Cys Val Cys Leu Ala Val Val Ile Thr Pro Thr
        35                  40                  45

Leu Trp Met Leu Ile Gly Val Val Ser Arg Ala Val Pro Val Phe His
    50                  55                  60

Trp Ser Val Leu Val Gln Asp Ser Gln Gly Asn Gly Gly Leu Arg
65                  70                  75                  80

Asn Ala Ile Ile Gly Thr Ala Val Leu Ala Ile Gly Val Ile Leu Val
                85                  90                  95

```
Gly Gly Thr Val Ser Val Leu Thr Gly Ile Tyr Leu Ser Glu Phe Ala
            100                 105                 110

Thr Gly Lys Thr Arg Ser Ile Leu Arg Gly Ala Tyr Glu Val Leu Ser
            115                 120                 125

Gly Ile Pro Ser Ile Val Leu Gly Tyr Val Gly Tyr Leu Ala Leu Val
130                 135                 140

Val Tyr Phe Asp Trp Gly Phe Ser Leu Ala Ala Gly Val Leu Val Leu
145                 150                 155                 160

Ser Val Met Ser Ile Pro Tyr Ile Ala Lys Ala Thr Glu Ser Ala Leu
                165                 170                 175

Ala Gln Val Pro Thr Ser Tyr Arg Glu Ala Ala Glu Ala Leu Gly Leu
            180                 185                 190

Pro Ala Gly Trp Ala Leu Arg Lys Ile Val Leu Lys Thr Ala Met Pro
            195                 200                 205

Gly Ile Val Thr Gly Met Leu Val Ala Leu Ala Leu Ala Ile Gly Glu
210                 215                 220

Thr Ala Pro Leu Leu Tyr Thr Ala Gly Trp Ser Asn Ser Pro Pro Thr
225                 230                 235                 240

Gly Gln Leu Thr Asp Ser Pro Val Gly Tyr Leu Thr Tyr Pro Ile Trp
                245                 250                 255

Thr Phe Tyr Asn Gln Pro Ser Lys Ser Ala Gln Asp Leu Ser Tyr Asp
            260                 265                 270

Ala Ala Leu Leu Leu Ile Val Phe Leu Leu Leu Ile Phe Ile Gly
            275                 280                 285

Arg Leu Ile Asn Trp Leu Ser Arg Arg Trp Asp Val
290                 295                 300

<210> SEQ ID NO 22
<211> LENGTH: 252
<212> TYPE: PRT
<213> ORGANISM: Pseudomonas

<400> SEQUENCE: 22

Met Ser Asn Ala Leu Leu Leu Gly Leu Ala Ala Val Thr Ala
1               5                   10                  15

Ser Phe Ala Trp Leu Glu Ile Asp Phe Gly Ala Leu Phe Gly Ala Asp
            20                  25                  30

Ser Leu Arg Gln Met Gly Asp Tyr Ala Ser Gly Phe Leu Ser Pro Asp
            35                  40                  45

Phe Ser Pro Ala His Leu Leu Ala Ile Gly Arg Gly Ala Leu Glu Thr
50                  55                  60

Leu Ala Met Ser Ala Ile Gly Thr Leu Leu Ala Leu Leu Gly Leu
65                  70                  75                  80

Leu Leu Ala Leu Pro Ala Ser Gly Arg Cys Gly Leu Pro Ala Asn Ala
                85                  90                  95

Ala Ala Arg Leu Leu Leu Asn Ala Leu Arg Ala Ile Pro Glu Leu Val
            100                 105                 110

Trp Ala Ala Leu Met Val Leu Ala Ala Gly Leu Gly Pro Asn Ala Gly
            115                 120                 125

Thr Leu Ala Leu Ala Leu His Thr Ala Gly Val Leu Gly Arg Leu Phe
130                 135                 140

Ala Glu Ala Leu Glu Asn Ile Pro Gly Glu Pro Ala Glu Ala Val Arg
145                 150                 155                 160

Leu Ala Gly Gly Gly Arg Val Ala Ala Phe Cys Tyr Gly Thr Leu Pro
                165                 170                 175
```

```
Gly Val Trp Pro Gln Leu Leu Ala Tyr Thr Leu Tyr Arg Trp Glu Asn
            180                 185                 190

Asn Ile Arg Met Ala Ser Val Leu Gly Phe Val Gly Ala Gly Gly Leu
            195                 200                 205

Gly Gln Met Leu Tyr Leu Ser Leu Ser Leu Phe Gln Glu Ala Gln Ala
            210                 215                 220

Ala Thr Val Ile Leu Ala Met Leu Ser Leu Val Leu Gly Val Asp Ala
225                 230                 235                 240

Leu Ser Gly Trp Gly Arg His Arg Trp Val Trp Asn
            245                 250

<210> SEQ ID NO 23
<211> LENGTH: 284
<212> TYPE: PRT
<213> ORGANISM: Thermocellum

<400> SEQUENCE: 23

Met Lys Lys Met Lys Arg Ile Val Leu Thr Val Thr Ile Leu Ala Leu
1               5                   10                  15

Phe Ile Thr Gly Cys Ala Thr Glu Asn Asn Asn Glu Ile Val Val Val
            20                  25                  30

Ser Arg Glu Glu Gly Ser Gly Thr Arg Gly Ala Phe Ile Glu Leu Phe
            35                  40                  45

Gly Ile Glu Glu Lys Asp Ser Asn Gly Asn Lys Val Asp Lys Thr Thr
            50                  55                  60

Asp Glu Ala Thr Val Val Asn Ser Thr Ser Val Val Met Thr Thr Val
65                  70                  75                  80

Ala Gly Asn Lys Asn Ser Ile Gly Tyr Ile Ser Leu Gly Ser Leu Asn
            85                  90                  95

Asp Thr Val Lys Ala Val Lys Val Asp Gly Val Glu Pro Thr Val Glu
            100                 105                 110

Asn Ile Lys Asn Asn Thr Tyr Lys Val Phe Arg Pro Phe Ile Ile Ala
            115                 120                 125

Thr Lys Glu Asn Pro Gly Glu Leu Thr Gln Asp Phe Ile Ser Phe Ile
            130                 135                 140

Leu Ser Ser Asp Gly Gln Lys Val Val Glu Glu Asn Ser Tyr Ile Ala
145                 150                 155                 160

Ala Ser Glu Lys Gly Pro Tyr Ser Ser Thr Lys Pro Ser Gly Lys Ile
            165                 170                 175

Val Ile Ala Gly Ser Ser Val Thr Pro Leu Met Glu Lys Leu Lys
            180                 185                 190

Glu Ala Tyr Leu Lys Val Asn Thr Asn Ala Glu Ile Glu Ile Gln Ala
            195                 200                 205

Ser Asp Ser Thr Thr Gly Met Lys Leu Ala Met Glu Gly Thr Cys Asp
            210                 215                 220

Ile Gly Met Ala Ser Arg Glu Leu Lys Glu Ser Glu Leu Lys Lys Leu
225                 230                 235                 240

Lys Pro Thr Val Ile Ala Met Asp Gly Leu Val Val Ile Val Asn Lys
            245                 250                 255

Glu Asn Pro Val Ser Asn Leu Thr Ser Asp Gln Ile Lys Gly Ile Phe
            260                 265                 270

Lys Gly Glu Ile Thr Ser Trp Asn Glu Val Ala Lys
            275                 280
```